United States Patent
Lawson et al.

(10) Patent No.: US 12,377,033 B2
(45) Date of Patent: *Aug. 5, 2025

(54) HAIR CARE COMPOSITION CONTAINING POLYMERIC COLORANT

(71) Applicant: Milliken & Company, Spartanburg, SC (US)

(72) Inventors: Richard Lawson, Greer, SC (US); Haihu Qin, Greer, SC (US); Eric Stephens, Spartanburg, SC (US); Wesley Freund, Simpsonville, SC (US); Sanjeev Dey, Spartanburg, SC (US)

(73) Assignee: Milliken & Company, Spartanbuurg, SC (US)

( * ) Notice: Subject to any disclaimer, the term of this patent is extended or adjusted under 35 U.S.C. 154(b) by 28 days.

This patent is subject to a terminal disclaimer.

(21) Appl. No.: 18/020,106

(22) PCT Filed: Sep. 10, 2021

(86) PCT No.: PCT/US2021/049776
§ 371 (c)(1),
(2) Date: Feb. 7, 2023

(87) PCT Pub. No.: WO2022/056205
PCT Pub. Date: Mar. 17, 2022

(65) Prior Publication Data
US 2023/0270651 A1    Aug. 31, 2023

Related U.S. Application Data

(60) Provisional application No. 63/077,737, filed on Sep. 14, 2020.

(51) Int. Cl.
| | |
|---|---|
| *A61Q 5/10* | (2006.01) |
| *A61K 8/45* | (2006.01) |
| *A61K 8/46* | (2006.01) |
| *A61K 8/49* | (2006.01) |
| *A61Q 5/02* | (2006.01) |
| *A61Q 5/06* | (2006.01) |
| *A61Q 5/12* | (2006.01) |

(52) U.S. Cl.
CPC ........... *A61K 8/4993* (2013.01); *A61K 8/45* (2013.01); *A61K 8/466* (2013.01); *A61Q 5/02* (2013.01); *A61Q 5/065* (2013.01); *A61Q 5/10* (2013.01); *A61Q 5/12* (2013.01); *A61K 2800/4322* (2013.01); *A61K 2800/4324* (2013.01)

(58) Field of Classification Search
CPC ........ A61K 8/4993; A61K 8/45; A61K 8/466; A61K 2800/4322; A61K 2800/4324; A61K 8/355; A61K 8/4913; A61K 8/4926; A61K 8/4946; A61K 8/4986; A61Q 5/02; A61Q 5/065; A61Q 5/10; A61Q 5/12

USPC .............................................................. 8/552
See application file for complete search history.

(56) References Cited

U.S. PATENT DOCUMENTS

| | | | |
|---|---|---|---|
| 3,192,117 A * | 6/1965 | Kaiser | C09B 1/22 8/405 |
| 5,688,291 A | 11/1997 | Said | |
| 5,789,560 A | 8/1998 | Etzbach | |
| 6,306,182 B1 | 10/2001 | Chan | |
| 7,056,355 B2 | 6/2006 | Pratt | |
| 7,083,655 B2 | 8/2006 | Pratt | |
| 7,189,265 B2 | 3/2007 | Said | |
| 7,553,337 B2 | 6/2009 | Pasquier | |
| 7,597,723 B2 * | 10/2009 | Moore | D06P 1/0052 8/525 |
| 8,785,361 B2 | 7/2014 | Sivik | |
| 9,068,081 B2 | 6/2015 | Torres | |
| 9,163,146 B2 * | 10/2015 | Torres | C09B 29/0059 |
| 9,820,922 B1 | 11/2017 | Singer | |
| 11,351,106 B2 | 6/2022 | Lawson | |
| 11,684,560 B2 | 6/2023 | Lawson | |
| 2002/0050012 A1 | 5/2002 | Orr | |
| 2002/0197223 A1 * | 12/2002 | Kimura | A61Q 5/10 424/408 |
| 2003/0037951 A1 | 2/2003 | Hulsmann | |
| 2003/0110977 A1 | 6/2003 | Batlaw | |
| 2004/0019982 A1 | 2/2004 | Pratt | |
| 2004/0143910 A1 | 7/2004 | Said | |
| 2005/0235433 A1 | 10/2005 | Rondeau | |

(Continued)

FOREIGN PATENT DOCUMENTS

| | | |
|---|---|---|
| CN | 101137345 A | 3/2008 |
| CN | 103210073 A | 7/2013 |
| CN | 103328584 A | 9/2013 |

(Continued)

OTHER PUBLICATIONS

STIC Search Report dated Jun. 6, 2024.*

(Continued)

*Primary Examiner* — Eisa B Elhilo
(74) *Attorney, Agent, or Firm* — Brenda D. Amidon

(57) ABSTRACT

This invention relates to a hair care composition that contains at least one hair care ingredient and at least one polymeric colorant. The invention also relates to a method for coloring human head or facial hair comprising the following steps: (a) providing a hair care composition that contains at least one poly(alkyleneoxy) substituted chromophore colorant; (b) applying the hair care composition to hair; and (c) allowing the hair care composition to contact the hair for a period of time.

39 Claims, No Drawings

(56) References Cited

U.S. PATENT DOCUMENTS

| | | |
|---|---|---|
| 2011/0154583 A1 | 6/2011 | Lewis |
| 2015/0080284 A1* | 3/2015 | Miracle ................ C11D 3/349 510/324 |

FOREIGN PATENT DOCUMENTS

| | | |
|---|---|---|
| CN | 105555934 A | 5/2016 |
| EP | 1366752 A1 | 12/2003 |
| EP | 3015134 | 5/2016 |
| EP | 3047010 A1 | 7/2016 |
| EP | 3021830 B1 | 4/2018 |
| EP | 3397236 A1 | 11/2018 |
| EP | 3397345 A1 | 11/2018 |
| EP | 3397346 A1 | 11/2018 |
| EP | 3019150 B1 | 4/2020 |
| FR | 2456764 A2 | 12/1980 |
| GB | 2217735 | 11/1989 |
| JP | 2008546662 | 12/2008 |
| JP | 2013534268 | 9/2013 |
| JP | 2023516791 | 4/2023 |
| JP | 2023542120 | 10/2023 |
| WO | 2006134051 A1 | 12/2006 |
| WO | 2009090122 A2 | 7/2009 |
| WO | 2012022709 A1 | 2/2012 |
| WO | 2015031418 A1 | 3/2015 |
| WO | 2015042209 A1 | 3/2015 |
| WO | 2017055254 A1 | 4/2017 |
| WO | 2017117522 A1 | 7/2017 |
| WO | 2017117543 A1 | 7/2017 |
| WO | 2017117552 A1 | 7/2017 |
| WO | 2017172516 A1 | 10/2017 |
| WO | 2017197099 A1 | 11/2017 |
| WO | 2022056204 | 3/2022 |

OTHER PUBLICATIONS

Dawson et al: "Poly(vinylamine hydrochloride). Synthesis and utilization for the preparation of water-soluble polymeric dyes", Journal of the American Chemical Society, American Chemical Society, vol. 98, No. 19, Sep. 15, 1976 (Sep. 15, 1976), pp. 5996-6000, XP002558622, ISSN: 0002-7863, DOI: 10.1021/JA00435A036.

Guthrie, J T: "Polymeric Colorants", Review of Progress in Coloration, Society of Dyers and Colourists. Bradford, GB, vol. 20, Jan. 1, 1990 (Jan. 1, 1990), pp. 40-52, XP000651083, ISSN: 0557-9325.

International Search Report and Written Opinion for App. No. PCT/US2021/049774, dated Feb. 2, 2022, 15 pages.

International Search Report and Written Opinion for App. No. PCT/US2021/049775, dated Feb. 7, 2022, 15 pages.

International Search Report and Written Opinion for App. No. PCT/US2021/049776, dated Feb. 10, 2022, 17 pages.

Shen et al: "Synthesis, Characterisation and properties of Ethoxylated Azo Dyes", Feb. 21, 2003 (Feb. 21, 2003), XP055880592, 6 pages, Retrieved from the Internet: URL:https://www.koreascience.or.kr/article/JAK0200311921587175.pdf [retrieved on Jan. 18, 2022].

STIC Search Report dated Feb. 4, 2022, 688 pages.

Wang Dongrui et al, "Amphiphilic azo polymers: Molecular engineering, self-assembly and photoresponsive properties", Progress in Polymer Science, Pergamon Press, Oxford, GB, (Jul. 16, 2012), vol. 38, No. 2, doi:10.1016/J.PROGPOLYMSCI.2012.07.003, ISSN 0079-6700, pp. 271-301, XP028980021.

* cited by examiner

HAIR CARE COMPOSITION CONTAINING POLYMERIC COLORANT

TECHNICAL FIELD

This invention relates to a hair care composition that contains at least one hair care ingredient and at least one polymeric colorant.

BACKGROUND

Various hair dyes have been invented as consumers desire to color their hair. Typically, there are two category of hair dyes. The first category is known as oxidative or permanent dye which is a form of pro-dye, which oxidizes during application to form color. A few well-known examples in this class are phenylenediamines and para-aminophenol, which are blended with additional coupling agents (such as resorcinol, m-aminophenol, and the like). The other category is often referred as non-oxidative or direct dyes. These dyes are pre-formed dye molecules. Examples in this category include Basic Red 76, Acid Violet 43, HC Blue 15, and HC Blue 16.

However, the current hair molecular dyes have drawbacks. The pre-formed dyes are conjugated, rigid organic compounds, and are often difficult to dissolve in the hair care compositions. The undissolved dyes can leave an uneven hue or sometimes color spots in treated hair. In addition, the toxicity of the hair dyes is also a concern. Additionally, the current direct dyes tend to wash off very quickly and thus are considered semi-permanent. Thus, improvement over current hair dyes are continuously needed. In this aspect, polymeric liquid colorants are superior than conventional hair dyes for they are easier to formulate and have less toxicity concerns as their higher molecular weight makes them hard to penetrate skin. Polymeric liquid colorants also appear to have superior wash performance compared to current dyes.

BRIEF SUMMARY

In one aspect, the invention relates to a method for coloring human head or facial hair comprising the following steps: (a) providing a hair care composition that contains at least one poly(alkyleneoxy) substituted chromophore colorant; (b) applying the hair care composition to hair; and (c) allowing the hair care composition to contact the hair for a period of time. The hair care composition may additionally contain at least one hair care ingredient.

The poly(alkyleneoxy) substituted chromophore colorant may be present in a concentration of from 0.001 to 20 wt. % of the composition, or even from 0.01 to 20 wt. % of the composition. The poly(alkyleneoxy) substituent of the chromophore is a polymeric substituent group that formed by removing a hydrogen or a group from a poly(alkyleneoxy) polymer comprised of alkyleneoxide residues having from 2 to 4 carbon atoms. Further, the average molecular weight of the poly(alkyleneoxy) substituent may be from 132 to 10,000. The chromophore colorant is selected from azo, carbazole, pyrazolone, cyanine, phthalocyanine, anthraquinone, aza[18]annulene, formazan copper complex, nitroso, nitro, diarylmethane, triarylmethane, xanthene, acridine, methine, thiazole, indamine, azine, oxazine, thiazine, quinoline, indigoid, indophenol, lactone, aminoketone, hydroxyketone, naphthalimide, and stilbene chromophores.

In one aspect of the invention, the chromophore has a structure of:

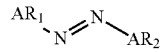

wherein $AR_1$ and $AR_2$ are independently selected from the group consisting of alkenyl groups, substituted alkenyl groups, aryl groups, substituted aryl groups, heteroaryl groups, and substituted heteroaryl groups; one of the $AR_1$ or $AR_2$ group can further substituted with another azo chromophore to form a bis azo.

In another aspect of the invention, the chromophore has a structure of:

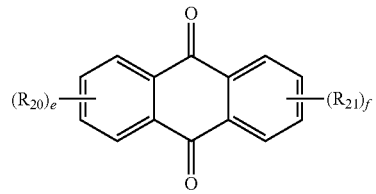

wherein e and f are independently integers from 0 to 4; each $R_{20}$ and $R_{21}$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, $—S(O)_2OH$, $—S(O)_2O^-[M^+]$, $—C(O)OR_5$, $—C(O)R_5$, $—C(O)NR_5R_6$, $—NR_5C(O)OR_6$, $—NR_5C(O)SR_6$, $—OR_5$, $—NR_5R_6$, $—S(O)_2R_5$, $—S(O)_2NR_5R_6$, and $—P(O)_2R_5$; M is a cation; $R_5$ and $R_6$ are independently selected from the group consisting of hydrogen, alkyl groups, substituted alkyl groups, aryl groups, and substituted aryl groups.

In a further aspect of the invention, the chromophore has a structure selected from:

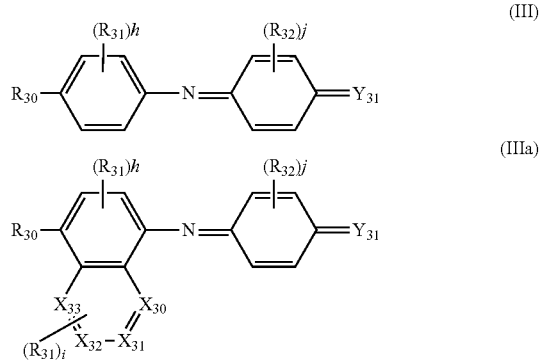

wherein h, i, and j are independently integers from 0 to 4; provided in structure IIIa h is an integer from 0 to 2. $Y_{31}$ is selected from the group consisting of $=O$, $=S$, $=NR_{34}$, and $=N^+R_{34}R_{35}$; $R_{30}$ is selected from the group consisting of $—O—$, $—S—$, $—OR_{36}$ and $—NR_{36}R_{37}$. Each $R_{34}$, $R_{35}$, $R_{36}$ and $R_{37}$ is independently selected from the group consisting of hydrogen, alkyl groups, substituted alkyl groups, aryl groups, substituted aryl groups, heteroaryl group, substituted heteroaryl group, acyl groups, $—C(O)OR_5$, $—C(O)R_5$, and $—C(O)NR_5R_6$. each $R_{31}$, $R_{32}$ and $R_{33}$ group is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_5$, —OR$_5$, —NR$_5$R$_6$, —S(O)$_2$R$_5$, —S(O)$_2$NR$_5$R$_6$, and —P(O)$_2$R$_5$; M is a cation; R$_5$ and R$_6$ are independently selected from the group consisting of hydrogen, alkyl groups, substituted alkyl groups, aryl groups, and substituted aryl groups. X$_{30}$, X$_{31}$, X$_{32}$, and X$_{33}$ are independently selected from the group consisting of a carbon atom and a nitrogen atom, provided no more than two of X$_{30}$, X$_{31}$, X$_{32}$, and X$_{33}$ are nitrogen atoms.

In yet another aspect of the invention, the chromophore has a structure of:

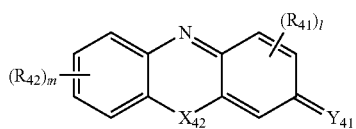

IV wherein X$_{42}$ is selected from the group consisting of an oxygen atom, a sulfur atom, SiR$_{45}$R$_{46}$, and NR$_{45}$. Y$_{41}$ is selected from the group consisting of =O, =S, =NR$_{46}$, and =N$^+$R$_{45}$R$_{46}$; R$_{45}$ and R$_{46}$ is selected from the group consisting of hydrogen, alkyl groups, substituted alkyl groups, aryl groups, substituted aryl groups, heteroaryl group, substituted heteroaryl group, —S(O)$_2$OH, —S(O)$_2$O$^-$[M$^+$], —C(O)OR$_5$, —C(O)R$_5$, and —C(O)NR$_5$R$_6$. l is an integer from 0 to 3 and m is an integer from 0 to 4. Each R$_{41}$ and R$_{42}$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —SR$_5$, —S(O)$_2$NR$_5$R$_6$, and —P(O)$_2$R$_5$; M is a cation; wherein at least one R$_{42}$ group is selected from the group consisting of —OR$_5$, —SR$_5$ and —NR$_5$R$_6$. R$_5$ and R$_6$ are independently selected from the group consisting of hydrogen, alkyl groups, substituted alkyl groups, aryl groups, and substituted aryl groups.

In another aspect of the invention, the chromophore has a structure of:

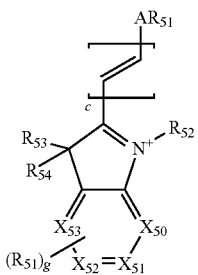

V wherein AR$_{51}$ is selected from the group consisting of alkenyl groups, substituted alkenyl groups, aryl groups, substituted aryl groups, heteroaryl groups, substituted heteroaryl groups; R$_{52}$ R$_{53}$ and R$_{54}$ are independently selected from the group consist of hydrogen and R$_5$; each R$_5$, is independently selected from halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$, M is a cation, provided R$_5$, is not a hydrogen; R$_5$ and R$_6$ are independently selected from the group consisting of hydrogen, alkyl groups, substituted alkyl groups, aryl groups, and substituted aryl groups; c is an integer from 1 to 10. X$_{50}$, X$_{51}$, X$_{52}$, and X$_{53}$ are independently selected from the group consisting of a carbon atom and a nitrogen atom, provided no more than two of X$_{50}$, X$_{51}$, X$_{52}$, and X$_{53}$ are nitrogen atoms; g is an integer from 1 to 4; and wherein the structure V optionally is present in an ionic form that accompanies its counter ion to maintain electric neutrality.

In one aspect of the invention, the chromophore has a structure of:

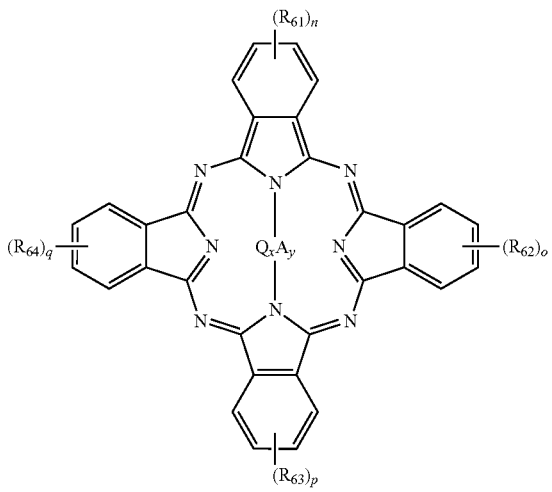

VI wherein each R$_{61}$, R$_{62}$, R$_{63}$, and R$_{64}$ group is independently selected halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4; R$_5$ and R$_6$ are independently selected from the group consisting of hydrogen, alkyl groups, substituted alkyl groups, aryl groups, and substituted aryl groups; Q is hydrogen, metal ion, or metalloids; A is an anion; x is a positive integer, and y is an integer including zero so that the divalent group -Q$_x$A$_y$- is neutral.

In yet a further aspect of the invention, the chromophore has a structure of:

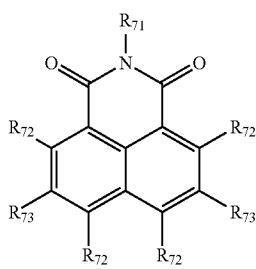

VII wherein each $R_{71}$, $R_{72}$ and $R_{73}$ group is independently selected hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)NR$_6$NR$_7$R$_8$, —NR$_5$C(O)SR$_5$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4; $R_5$, $R_6$, $R_7$ and $R_8$ are independently selected from the group consisting of hydrogen, alkyl groups, substituted alkyl groups, aryl groups, and substituted aryl groups, provided at least one $R_{72}$ groups is —OR$_5$ or —NR$_5$R$_6$ group.

In another aspect of the invention, the chromophore has a structure selected from:

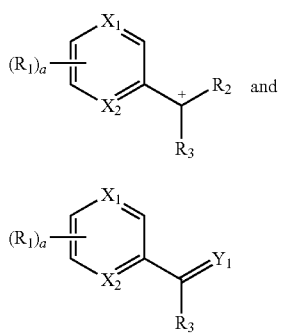

VIII

VIIIa wherein $X_1$ and $X_2$ are selected from the group consisting of a carbon atom and a nitrogen atom; a is an integer from 0 to 5, provided a is an integer from 0 to 4 when one of $X_1$ and $X_2$ is a nitrogen atom and a is an integer from 0 to 3 when both $X_1$ and $X_2$ are nitrogen atoms; each $R_1$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups; $R_2$ and $R_3$ is selected from the group consisting of alkenyl groups, substituted alkenyl groups, aryl groups, substituted aryl groups, heteroaryl groups, and substituted heteroaryl groups; $Y_1$ is selected from the group consisting of =O, =S, =NR$_5$, and =N$^+$R$_5$R$_6$; wherein the structures VIII and VIIIa independently and optionally may exist in an ionic form that accompanies its counter ion to maintain electric neutrality.

In a further aspect of the invention, the chromophore has a structure of:

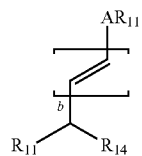

IX wherein AR$_{11}$ is selected from the group consisting of alkenyl groups, substituted alkenyl groups, aryl groups, substituted aryl groups, heteroaryl groups, and substituted heteroaryl groups; $R_{11}$ and $R_{14}$ are independently selected from the group consist of hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups; b is an integer from 1 to 10.

In another aspect of the invention, at least 50 molar % of the poly(alkyleneoxy) substituted chromophore colorant has a molecular weight less than 5000, or even less than 2000. In addition, the poly(alkyleneoxy) substituted chromophore colorants contain monomer residues and at least 75% of the monomer residues in the poly(alkyleneoxy) substituent are selected from —CH$_2$CH$_2$O— and —CH$_2$CH(CH$_3$)O—. In a further aspect of the invention, the poly(alkyleneoxy) substituted chromophore colorants contain monomer residues and at least 75% of monomer residues in the poly(alkyleneoxy) substituent are —CH$_2$CH$_2$O—.

In a further aspect of the invention, the hair care composition is a non-oxidative hair coloring cream. The non-oxidative hair coloring cream may be a semi-permanent hair coloring cream or a temporary hair coloring cream.

In yet another aspect of the invention, the hair care composition is an oxidative hair coloring cream. The oxidative hair coloring cream may be a demi-permanent hair coloring cream or a permanent hair coloring cream.

In a further aspect of the invention, the hair care composition is a shampoo or a conditioner.

DETAILED DESCRIPTION

The invention described herein is a hair care composition containing at least one hair care ingredient and at least one polymeric colorant. The polymeric colorant-containing hair care composition is suitable for direct application to hair (such as human hair, animal hair, and the like) and provides improvements in stability and shading over prior art hair dyes.

As used herein, the term "hair" is intended to include keratin fiber that are attached to a living organism, such as human head hair, human facial hair, animal hair, and the like.

As used herein, the term "alkoxy" is intended to include $C_1$-$C_6$ alkoxy and alkoxy derivatives of polyols having repeating units such as butylene oxide, glycidol oxide, ethylene oxide or propylene oxide.

As used herein, the terms "polyalkyleneoxy" and "polyoxyalkylene," as used interchangeably herein, generally refer to molecular structures containing the following repeating units: $-CH_2CH_2O-$, $-CH_2CH_2CH_2O-$, $-CH_2CH_2CH_2CH_2O-$, $-CH_2CH(CH_3)O-$, $-CH_2CH_2CH(CH_3)O-$, and any combinations thereof. Furthermore, the polyoxyalkylene constituent may be selected from the group consisting of one or more monomers selected from $C_{2-20}$ alkylene oxide, glycidol, and mixtures thereof.

As used herein, unless otherwise specified, the terms "alkyl" and "alkyl capped" are intended to include $C_2$ to $C_{100}$ alkyl groups, $C_2$ to $C_{50}$ alkyl groups, $C_5$-$C_{25}$ alkyl groups, or even $C_{10}$-$C_{20}$ alkyl groups.

As used herein, unless otherwise specified, the term "aryl" is intended to include $C_5$-$C_{18}$ aryl groups and, in one aspect, $C_5$-$C_{12}$ aryl groups.

As used herein, unless otherwise specified, the term "arylalkyl" is intended to include $C_1$-$C_{18}$ arylalkyl groups and, in one aspect, $C_1$-$C_6$ arylalkyl groups.

As used herein, unless otherwise specified, the term "alkanoyl" refers to univalent groups of the formula $-C(O)R^a$, where $R^a$ is an alkyl group, preferably a $C_3$-$C_{29}$ alkyl group.

As used herein, unless otherwise specified, the term "alkenyl" refers to univalent groups derived from acyclic olefinic hydrocarbons by removal of a hydrogen atom from any carbon atom. In the context of this definition, the term "acyclic olefinic hydrocarbons" refers to acyclic hydrocarbons containing one or more carbon-carbon double bonds.

A used herein, unless otherwise specified, the term "alkenoyl" refers to univalent groups of the formula $-C(O)R^b$, where $R^b$ is an alkenyl group, preferably a $C_3$-$C_{29}$ alkenyl group.

A used herein, unless otherwise specified, the term "aroyl" refers to univalent groups of the formula $-C(O)R^c$, where $R^c$ is an aryl group, preferably a $C_6$-$C_{10}$ aryl group.

The terms "ethylene oxide," "propylene oxide" and "butylene oxide" may be shown herein by their typical designation of "EO," "PO" and "BO," respectively.

All percentages and ratios are calculated by weight unless otherwise indicated. All percentages and ratios are calculated based on the total composition unless otherwise indicated.

The hair care compositions may be in any suitable physical form for application to hair including, but not limited to, liquids, creams, sprays, conditioners, gels, mousses, and the like. Hair care compositions are intended to include, but are not limited to, oxidative hair creams, non-oxidative hair creams, bleaching compositions, shampoos, conditioners, and any other compositions useful as a vehicle for applying the ingredients described herein to hair. Further details and examples of suitable physical forms and vehicles for application of the composition of the present invention may also be found in U.S. Pat. No. 9,820,922 to Singer et al.

In the present invention, the hair care composition includes at least one hair care ingredient. Hair care ingredients include, for example but not limited to, emollient oils, surfactants, nonionic surfactants, anionic surfactants, cationic, zwitterionic or betaine surfactants, polar solvents, chelating agents, pH adjusters, conditioning agents and mixtures thereof. Oxidizing agents may also be included in oxidizing formulations. Further, oxidizing agents may be excluded in non-oxidizing formulations.

The hair care composition of the invention is generally aqueous based comprising from about 0.01-99%, preferably from about 0.1-98%, more preferably from about 45 to 95% by weight of the total composition of water.

Hair care composition may include for example, hair shampoos which are based on classic anionic, amphoteric, zwitterionic, nonionic, and/or cationic surfactants. Suitable commercial shampoos clean the hair and remove sebaceous residues and/or residues of styling agents and other impurities from the hair surface and the scalp.

Hair care composition may also include hair conditioners. Hair conditioning is understood by those skilled in the art to mean the treatment of hair with caring so-called rinse-off formulations (i.e. formulations which are rinsed off) or so-called leave-on formulations (i.e. Formulations which remain on the hair without being rinsed off), particularly with caring shampoos or conditioners. This treatment leads in particular to easier combability of the hair in the wet and dry state, both along the lengths and at the tips (detanglability), to improved tactile properties such as smoothness, softness and suppleness and also to more hair shine, less electrostatic charge and improved ease of styling. Overall, a cared-for and healthy overall condition of the hair is thus achieved by the conditioning.

Emollient Oils

If desired the hair cream composition may contain one or more emollient oils. Such oils will provide a conditioning effect to the hair. If present, such oils may range from about 0.001 to 45% preferably from about 0.01 to 40%, more preferably from about 0.1 to 35% by weight of the total composition. Suitable oils include silicones such as dimethicone, phenyl silicones, fatty alkyl silicones such as cetyl or stearyl dimethicone, or silicone surfactants which are generally referred to as dimethicone copolyols, or cetyl dimethicone copolyol. Also suitable are various animal, vegetable, or mineral oils derived from plants or animals, or synthetic oils. Examples include oils from sunflower, castor seeds, orange, lemon, jojoba, mineral oil, and the like. Common other examples would include cetearyl alcohol, lauryl alcohol, myristyl alcohol, lanolin alcohol, coconut alcohol, and the like.

Surfactants

The oxidative dye composition may comprise one or more surfactants. Suitable surfactants include anionic surfactants, nonionic surfactants, amphoteric surfactants, and the like. If present, surfactants may range from about 0.001-50%, preferably about 0.005-45%, more preferably about 0.1-40% by weight of the first composition.

Nonionic Surfactants

Examples of nonionic surfactants include alkoxylated alcohols or ethers, alkoxylated carboxylic acids, sorbitan derivatives, and the like. Alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2-30, which is formed by the reaction of stearyl alcohol and ethylene oxide where the number of repeating ethylene oxide units is 2 to 30; laureth 2-30, which is formed by the reaction of lauryl alcohol and ethylene oxide where the number of repeating ethylene oxide units is 2 to 30; Oleth 2-30 which is formed by the reaction of oleyl alcohol and ethylene oxide where the number of repeating ethylene oxide units is 2 to 30; Ceteareth 2-100, formed by the reaction of a mixture of cetyl and stearyl alcohol with ethylene oxide, where the number of repeating ethylene oxide units in the molecule is 2 to 100;

Ceteth 1-45 which is formed by the reaction of cetyl alcohol and ethylene oxide, and the number of repeating ethylene oxide units is 1 to 45, and so on. Particularly preferred is where the nonionic surfactant is steareth-20 or cetearth-20. Also suitable are alkyoxylated carboxylic acids, which are formed by the reaction of a carboxylic acid with an alkylene oxide or with a polymeric ether.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on. In one preferred embodiment Polysorbate 20 is preferred.

Anionic Surfactants

The hair cream composition may optionally contain one or more anionic surfactants. Preferred ranges of anionic surfactant are about 0.01-25%, preferably 0.5-20%, more preferably 1-15% by weight of the total oxidative composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula: $R_1$—$SO_3$-M wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide, or fatty acids reacts with alkanolamines or ammonium hydroxides. The fatty acids may be derived from coconut oil, for example. Examples of fatty acids also include lauric acid, stearic acid, oleic acid, palmitic acid, and so on.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones, which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula: wherein $R_1$ is a $C_{8-24}$ alkyl or alkenyl radical, preferably $C_{10-18}$; $R_2$ is H, $C_{1-4}$ alkyl, phenyl, or —$CH_2OOOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Cationic, Zwitterionic or Betaine Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula R—$NH(CH_2)_n$COOM or iminodialkanoates of the formula: R—$[(CH_2)_m$COOM$]_2$ and mixtures thereof, wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates. Zwitterionic surfactants are also suitable for use in the compositions of the invention and include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like. Particularly preferred is cocamidopropylbetaine.

Polar Solvents

The hair cream composition may also comprise a variety of nonaqueous polar solvents other than water, including mono-, di-, or polyhydric alcohols, and similar water soluble ingredients. If present, such polar solvents may range from about 0.01-25%, preferably about 0.05-15%, more preferably about 0.1-10% by weight of the first composition of polar solvent. Examples of suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glycerin, glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like.

Chelating Agents

The oxidative dye composition may optionally contain 0.0001-5%, preferably 0.0005-3%, more preferably 0.001-2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

pH Adjusters

It may also be desirable to add small amounts of acids or bases to adjust the pH of the oxidative dye composition to the desired pH range. Suitable acids include hydrochloric acid, phosphoric acid, etidronic acid, and the like. Suitable bases include sodium hydroxide, ammonium hydroxide, potassium hydroxide, and the like. Also suitable are primary, secondary, or tertiary amines or derivative thereof such as aminomethyl propanol, monoethanolamine, and the like. Phosphate salts such as potassium phosphate, disodium phosphate, and the like may also be used. Suggested ranges of pH adjusters are from about 0.00001-8%, preferably about 0.00005-6%, more preferably about 0.0001-5% by weight of the total composition.

Conditioning Agents

Hair cream compositions may also include a hair conditioning agent. Suitable conditioning agents for use herein include, but are not limited to, cationic surfactants, insoluble silicones, non-volatile hydrocarbons, non-volatile hydrocarbon esters, and mixtures thereof.

Preferred conditioning agents for use herein include cationic surfactants, cationic polymers, insoluble silicone conditioning agents, amino functionalized silicones and saturated C14-C22 straight chain fatty alcohols and mixtures thereof.

When present, the insoluble silicone conditioning agents are present at a level of from about 0.1 to 10%, preferably from about 0.1% to about 5%, more preferably from about 1% to about 3% by weight of composition. Suitable insoluble silicones include polyalkyl siloxanes, polyaryl siloxanes, polyalkylaryl siloxanes, polether siloxane copolymers, and mixtures thereof.

Other Additional Components

The compositions of the present invention typically further comprise a number of other components commonly utilized in hair care compositions such as shampoos, conditioners, styling aids and colorants which are well known to those skilled in the art such as for example thickeners and diluents. Additionally, a number of optional materials can be added to the compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl® K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; H2O2 stabilizers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and >hydroxybenzoates; moisturizing agents such as hyaluronic acid, chitin, and starch-grafted sodium polyacrylates as well as methyl cellulose, starch, higher fatty alcohols, paraffin oils, fatty acids and the like; solvents; antibacterial agents; low temperature phase modifiers such as ammonium ion sources (e.g. NH4Cl); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilizers such as water soluble sources of calcium or borate species; TiO2 and TiO2-coated mica; perfumes and perfume solubilizers; and zeolites and derivatives thereof and metal ion sequestrants such as polycarboxylates, amino polycarboxylates, polyphosphonates, amino polyphosphonates etc. and water softening agents such as sodium citrate, inorganic peroxygen oxidizing agents and enzymes.

Oxidizing Agent Composition

In addition, the aqueous hair cream composition may also comprise an oxidizing agent. Most often the aqueous oxidizing agent used is hydrogen peroxide, but other peroxides or oxidizing agents may be used such as calcium peroxide. Preferably the hydrogen peroxide concentration in the aqueous oxidizing agent composition ranges from about 10 to 40 volume, that is the amount of hydrogen peroxide that is present in the composition on a volume basis.

Additional suitable oxidizing agents (also referred to herein as "bleaching agents") include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate, sodium percarbonate, sodium persulfate, and potassium persulfate are particularly preferred. Mixtures of any convenient hydrogen peroxide sources can also be used.

Compositions of the present invention may also comprise as the bleaching agent a chlorine-type bleaching material. Such agents are well known in the art and include for example sodium dichloroisocyanurate ("NaDCC").

In one aspect of the invention, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide source leads to the in situ production of the peracid corresponding to the bleach activator. Various non-limiting examples of activators are disclosed in U.S. Pat. Nos.

5,576,282; 4,915,854 and 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 11 are those selected having an OBS or VL leaving group.

Preferred hydrophobic bleach activators include, but are not limited to, nonanoyloxybenzenesulphonate (NOBS); 4-[N-(nonanoyl) amino hexanoyloxy]-benzene sulfonate sodium salt (NACA-OBS), an example of which is described in U.S. Pat. No. 5,523,434; dodecanoyloxybenzenesulphonate (LOBS or $C_{12}$-OBS); 10-undecenoyloxybenzenesulfonate (UDOBS or $C_{11}$-OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., and copending patent application Ser. No. 08/064,564, all of which are incorporated herein by reference.

Quaternary substituted bleach activators may also be included. The present compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Additional bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl) oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)=N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 11.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, may also be useful herein, especially the acyl caprolactams (see for example WO 94-28102 A) and acyl valerolactams (see U.S. Pat. No. 5,503,639 to Willey et al. incorporated herein by reference).

Organic peroxides, especially diacyl peroxides, may also be suitable for use. These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn^{IV}_2$(u-O)$_3$(1,4,7-trimethyl-1,4,7-triazacyclononane)$_2$(PF$_6$)$_2$, $Mn^{III}_2$(u-O)$_1$(u-OAc)$_2$(1,4,7-trimethyl-1,4,7-triazacyclononane)$_2$(ClO$_4$)$_2$, $M^{IV}_4$(u-O)$_6$(1,4,7-triazacyclononane)$_4$(ClO$_4$)$_4$, $Mn^{III}Mn^{IV}_4$(u-O)$_1$(u-OAc)$_2$-(1,4,7-trimethyl-1,4,7-triazacyclononane)$_2$(ClO$_4$)$_3$, $Mn^{IV}$(1,4,7-trimethyl-1,4,7-triazacyclononane)-(OCH$_3$)$_3$(PF$_6$), and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorq. Bioinorg. Mech.*, (1983), 2, pages 1-94. The most preferred cobalt catalyst useful herein are cobalt pentaamine acetate salts having the formula [Co(NH$_3$)$_5$OAc]T$_y$, wherein "OAc" represents an acetate moiety and "T$_y$" is an anion, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co—(NH$_3$)$_5$OAc](BF$_4$)$_2$; and [Co(NH$_3$)$_5$OAc](NO$_3$)$_2$(herein "PAC").

These cobalt catalysts are readily prepared by known procedures, such as taught for example in U.S. Pat. Nos. 6,302,921; 6,287,580; 6,140,294; 5,597,936; 5,595,967; and 5,703,030; in the Tobe article and the references cited therein; and in U.S. Pat. No. 4,810,410; *J. Chem. Ed.* (1989), 66 (12), 1043-45; The Synthesis and Characterization of Inorganic Compounds, W. L. Jolly (Prentice-Hall; 1970), pp. 461-3; *Inorg. Chem.*, 18, 1497-1502 (1979); *Inorg. Chem.*, 21, 2881-2885 (1982); *Inorg. Chem.*, 18, 2023-2025 (1979); Inorg. Synthesis, 173-176 (1960); *and Journal of Physical Chemistry*, 56, 22-25 (1952).

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of macrocyclic rigid ligands which are suitable for use in the invention compositions can in general include known compounds non-limitingly illustrated by any of the following:

Dichloro-5,12-dimethyl-1,5,8,12-tetraazabicyclo[6.6.2] hexadecane Manganese(II)

Dichloro-5,12-diethyl-1,5,8,12-tetraazabicyclo[6.6.2]hexadecane Manganese(II)

Diaquo-5,12-dimethyl-1,5,8,12-tetraazabicyclo[6.6.2]hexadecaneManganese(II) Hexafluorophosphate Diaquo-5,12-diethyl-1,5,8,12-tetraazabicyclo[6.6.2]hexadecaneManganese(II) Hexafluorophosphate Aquo-hydroxy-5,12-dimethyl-1,5,8,12-tetraazabicyclo [6.6.2]hexadecane Manganese(II) Hexafluorophosphate Diaquo-5,12-dimethyl-1,5,8,12-tetraazabicyclo[6.6.2]hexadecaneManganese(II) Tetrafluoroborate Dichloro-5,12-dimethyl-1,5,8,12 tetraazabicyclo[6.6.2] hexadecane Manganese(II) Hexafluorophosphate Dichloro-5,12-diethyl-1,5,8,12-tetraazabicyclo[6.6.2]hexadecaneManganese(III) Hexafluorophosphate Dichloro-5,12-di-n-butyl-1,5,8,12-tetraaza bicyclo[6.6.2] hexadecane Manganese(II)

Dichloro-5,12-dibenzyl-1,5,8,12-tetraazabicyclo[6.6.2] hexadecaneManganese(II)

Dichloro-5-n-butyl-12-methyl-1,5,8,12-tetraaza-bicyclo [6.6.2]hexadecane Manganese(II)

Dichloro-5-n-octyl-12-methyl-1,5,8,12-tetraaza-bicyclo [6.6.2]hexadecane Manganese(II)

Dichloro-5-n-butyl-12-methyl-1,5,8,12-tetraaza-bicyclo [6.6.2]hexadecane Manganese(II).

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

The compositions herein may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in accordance with the present invention are cationic imines, zwitterionic imines, anionic imines and/or polyionic imines having a net charge of from about +3 to about –3, and mixtures thereof. These imine bleach boosting compounds of the present invention include those of the general structure:

[A]

where $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source that could be employed in the present invention may comprise any of these well known sources, including peroxygen compounds as well as compounds, which under consumer use conditions, provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. The bleach boosting compounds, when present, are preferably employed in conjunction with a peroxygen source in the bleaching systems of the present invention.

Also suitable as bleaching agents are preformed peracids. The preformed peracid compound as used herein is any convenient compound which is stable and which under consumer use conditions provides an effective amount of peracid or peracid anion. The preformed peracid compound may be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

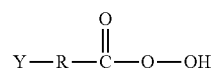

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

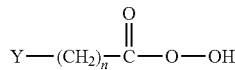

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

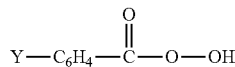

wherein Y can be, for example, hydrogen, alkyl, alkylhalogen, halogen, C(O)OH or C(O)OOH.

Typical monoperoxy acids useful herein include alkyl and aryl peroxyacids such as:
(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);
(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);
(iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxyacids, such as:
(i) 1,12-diperoxydodecanedioic acid;
(ii) 1,9-diperoxyazelaic acid;
(iii) diperoxybrassylic acid; diperoxysebacic acid and diperoxyisophthalic acid;
(iv) 2-decyldiperoxybutane-1,4-dioic acid;
(v) 4,4'-sulfonylbisperoxybenzoic acid.

Such bleaching agents are disclosed in U.S. Pat. No. 4,483,781 to Hartman and U.S. Pat. No. 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, DE can also be employed as a suitable source of peroxymonosulfuric acid. PAP is disclosed in, for example, U.S. Pat. Nos. 5,487,818; 5,310,934; 5,246,620; 5,279,757 and 5,132,431.

Photobleaches may also be suitable for use in the compositions of the present invention and include, but are not limited to, the photobleaches described in U.S. Pat. Nos. 4,217,105 and 5,916,481.

Enzymatic systems may be used as bleaching agents. The hydrogen peroxide may also be present by adding an enzymatic system (i.e. an enzyme and a substrate therefore) which is capable of generating hydrogen peroxide. Such enzymatic systems are disclosed in EP Patent Application 91202655.6 filed Oct. 9, 1991.

The present invention compositions and methods may utilize alternative bleach systems such as ozone, chlorine dioxide and the like. Bleaching with ozone may be accomplished by introducing ozone-containing gas having ozone content from about 20 to about 300 $g/m^3$ into the solution that is to contact the hair. The gas:liquid ratio in the solution should be maintained from about 1:2.5 to about 1:6. U.S. Pat. No. 5,346,588 describes a process for the utilization of ozone as an alternative to conventional bleach systems and is herein incorporated by reference.

Colorants

The coloring compositions of the present disclosure may optional contain one or more colorant other than polymeric colorants. These color compound can be chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2.3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N, N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N, N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-1, N,N'-bis(.beta.-hydroxyethyl)-N,N'-bis(4'-aminophenyl)ethylenediamine, N,N-bis(4-aminophenyl)tetramethylenediamine, N,N'-bis(.beta.-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid. Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more (Ci-$C_6$-alkyl, such as di(C1-C4)alkylpiperazinium; or (c) one (Ci-C6)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists. Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol--3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions according to the present disclosure may optionally comprise one or more couplers advantageously chosen from those conventionally used in the dyeing or coloring of keratin fibers. Among these couplers, mention may be made especially of meta-phenylenediamines, meta-aminophenols, meta-diphenols, naphthalene-based couplers and heterocyclic couplers, and also the addition salts thereof. Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates. The oxidation base(s) each advantageously represent from 0.001% to 10% by weight relative to the total weight of the composition, and preferably from 0.005% to 5% by weight relative to the total weight of the compositions of the present disclosure. The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may comprise b) one or more synthetic or natural direct dyes or pigment. Suitable dyes or pigment includes but not limited to those listed in Annex IV in regulation (EC) No 1223/2009 of the European parliament and of the council. Examples of suitable direct dyes that may be mentioned include azo direct dyes; (poly)methine dyes such as cyanins, hemicyanins and styryls; carbonyl dyes; azine dyes; nitro(hetero)aryl dyes; tri(hetero)aryl methane dyes; porphyrin dyes; phthalocyanin dyes, and natural direct dyes, alone or as mixtures. Many direct dyes are cationic direct dyes. Mention may be made of the hydrazono cationic dyes, the azo cationic dyes, and the diazo cationic dyes. Particular examples include Basic Red 51, Basic Yellow 87 and Basic Orange 31 or derivatives thereof: Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices, or extracts may also be used. When they are present, the direct dye(s) more particularly represent from 0.001% to 10% by weight and preferably from 0.005% to 5% by weight of the total weight of the compositions of the present disclosure.

Alkalizing Agents

The hair care composition may have a pH that is alkaline. Exemplary pH's include 7, 8, 9, 10, 11, 12, 13 or 14. In some embodiments, the pH of the hair coloring composition may range from about 7, 8, or 9 to about 9, 10, 11 or 12. The alkalinity of the hair coloring composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., $NH_4OH$). The one or more alkalizing agents may be present in amounts ranging from greater than about 0, or from 1, 2, 3, 4, 5, 10 to about 5, 10, 13, 15, 18, 20, 25 or 30% by weight of the total composition.

The hair care compositions may be in the form of a cream, an aqueous solution, a uniform dispersion, or a suspension of surfactant, or even a liquid. Such compositions will be acceptably phase stable and will typically have a viscosity which ranges from about 1 to 1,000,000 cps, more preferably from about 10 to 100,000, most preferably from 100 to 20,000 cps. For purposes of this invention, viscosity is measured with a Brookfield LVDV-II+ viscometer apparatus at room temperature at 1 rpm with corresponding cup and spindle.

The hair care composition of the present invention contains at least one poly(alkyleneoxy) substituted chromophore colorant. The term "poly(alkyleneoxy) substituted chromophore colorant" generally refers to a colorant having at least one chromophore portion attached to at least one oligomeric or polymeric poly(alkyleneoxy) chain, wherein the chain has at least two repeating units, and preferably at least three repeating units. The oligomeric or polymeric substituent can be bound to the chromophore portion via any suitable means, such as a covalent bond, an ionic bond, or suitable electrostatic interaction. Generally, the polymeric colorant may be characterized by having an absorbance in the range of between about 300 nanometers and about 900 nanometers, as measured by UV-vis spectroscopy. In one aspect of the invention, the polymeric colorant has a maximum absorbance in the range from 400 nanometers to 700 nanometers.

As a function of its manufacturing process, the polymeric colorant has a molecular weight that is typically represented as a molecular weight distribution. Accordingly, the molecular weight of the polymeric colorant is generally reported as an average molecular weight, as determined by its molecular weight distribution.

The chromophore portion of the polymeric colorant may vary widely and may include compounds characterized in the art as dyestuffs or as pigments. The actual group used will depend to a large extent upon, for instance, the desired color, colorfastness, and stability characteristics. The chromophore portion may be attached to at least one polyalkyleneoxy-substituent through a suitable linking moiety of nitrogen, oxygen, sulfur, etc.

In one aspect, the polymeric colorant be a neutral or an uncharged molecule. In a further aspect, the polymeric colorant may be nonionic, anionic, or cationic. The polymeric colorant may contain a chromophore group that has both positive and negative charges. Further, the polymeric colorant may be zwitterionic or amphoteric.

Examples of chromophore include nitroso, nitro, azo (including monoazo, bisazo, trisazo, tetrakisazo, and polyazo), formazan, azomethine and metal complexes thereof), stilbene, bis-stilbene, biphenyl, oligophenethylene, fluorene, coumarin, napthalamide, diarylmethane, triarylmethane, xanthene, acridine, quinoline, methine (including polymethine), thiazole, indamine, indophenol, azine, thiazine, oxazine, aminoketone, hydroxyketone, anthraquinone (including anthrapyrazolines, anthrone, anthrapyridone, anthrapyrimidine, flavanthrone, pyranthrone, benzanthrone, perylene, perinone, naphthalimide and other structures formally related to anthraquinone), indigoid (including thioindigoid), phthalocyanine chromophore groups, and mixtures thereof. In one aspect of the invention, the polymeric colorant is an azo polymeric colorant.

Examples of suitable polymeric chains are polyalkyleneoxy chains. The term "polyalkyleneoxy," as used herein, generally refers to molecular structures containing the following repeating units: —$CH_2CH_2O$—, —$CH_2CH_2CH_2O$—, —$CH_2CH_2CH_2CH_2O$—, —$CH_2CH(CH_3)O$—, —$CH_2CH$ (CH₂CH₃)O—, CH₂CH₂CH(CH₃)O—, CH₂CH(O—)(CH₂O—), and any combinations thereof.

Typical of such groups which may be attached to the chromophore group are the polymeric epoxide groups, such as the polyalkylene oxide groups and copolymer groups thereof. Typical polyalkylene oxides and copolymers of same which may be employed to provide the colorants include those made from alkylene oxide monomers containing from two to twenty carbon atoms, or more preferably, from two to six carbon atoms. Examples include: polyethylene oxides; polypropylene oxides; polybutylene oxides; oxetanes; tetrahydrafurans; copolymers of polyethylene oxides, polypropylene oxides and polybutylene oxides; and other copolymers including block copolymers, in which a majority of the polymeric substituent is polyethylene oxide, polypropylene oxide and/or polybutylene oxide. Further, such polyalkyleneoxy group may have an average molecular weight in the range of from about 132 to about 10,000, preferably from about 176 to about 5000.

It is to be understood that because the colorants may or may not be chemically bound to ingredients comprising the hair care composition, the precise chemical identity of the end group on the polyalkyleneoxy group may not be critical insofar as the proper functioning of the colorant is concerned in the composition. With this consideration in mind, certain most preferred colorants will be defined wherein certain end groups will be identified. Such recitation of end groups is not to be construed as limiting the invention in its broader embodiments in any way. According to such a most preferred embodiment the colorants may be characterized as follows:

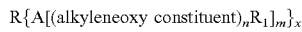

wherein R is an organic chromophore group, A is a linking chemical bond (including single, double, and triple bond) or a moiety in said organic chromophore group independently selected from the group consisting of —N═, —O—, —SO₂—, —SO₂N═, or —CO₂—, the alkylene moiety of the alkyleneoxy constituent contains from 2 to about 4 carbon atoms, n is an integer independently selected from 0 to about 230, while at least one n is no less than two. m is 1 when A is —O—, —SO₂—, —CO₂— and 1 or 2 when A is —N═ and —SO₂N═, x is an integer of from 1 to 5, and the sum of all the n values is from 2 to about 230, and R₁ is independently selected from hydrogen, alkyl group and the group consisting of:

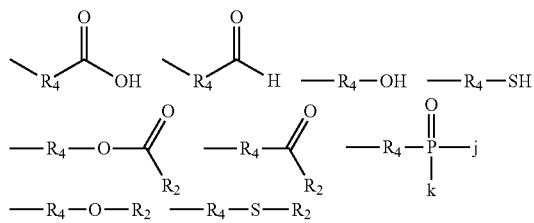

wherein R₂ is H, an alkyl radical containing up to about 20 carbon atoms or carboxy-terminated alkyl radical containing up to about 20 carbon atoms, j and k are OH, OM or OR₃ wherein M is a cation moiety of an alkali metal, an alkaline earth metal, transition metal, e.g., nickel, etc. or ammonium, and R₃ is an alkyl radical containing up to about 20 carbon atoms, and R₄ is selected from —CH₂—, —CH₂CH₂—, CH₂CH₂CH₂—, —CH₂CH₂CH₂CH₂—, —CH₂CH(CH₃)—, —CH₂CH(CH₂CH₃)—, CH₂CH₂CH(CH₃)—, CH₂CH(OR₁)(CH₂)—

The oligomeric constituent can be any suitable constituent including, but not limited to, oligomeric constituents selected from the group consisting of (i) oligomers comprising at least two monomers, or repeating units, selected from the group consisting of C₂-C₂₀ alkyleneoxy groups, glycidol groups, and glycidyl groups, (ii) aromatic or aliphatic oligomeric esters conforming to structure (1):

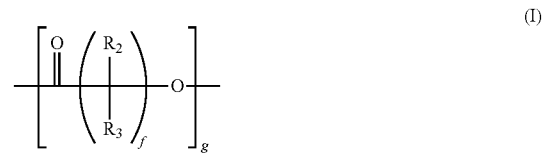

and (iii) combinations of (i) and (ii). In structure (1), R₂ and R₃ are independently selected from the group consisting of hydrogen and C₁-C₁₀ alkyl groups, f is an integer between and including 1 and 10, and g is any positive integer or fraction between and including 1 and 20. As will be understood by those of ordinary skill in the art, suitable values for g include both integers and fractions because the length of the oligomeric constituent on the individual polymeric colorant molecules may vary. Thus, the value for g represents an average length of the ester chain for a given sample or collection of polymeric colorant molecules. In certain embodiments, the polymeric colorant can comprise one or more oligomeric constituents consisting of two or more ethylene oxide monomer groups.

The polymeric colorant may be alkoxylated. Alkoxylation is carried out by procedures well-known to those skilled in the art (see, for example, U.S. Pat. Nos. 4,137,243; 5,082,938; 5,135,972; 5,591,833; 6,593,483; 7,587,857; 9,056,963; and 9,068,081).

Exemplary polymeric colorants include Liquitint® polymeric colorants, Cleartint® polymeric liquid concentrate colorants, Reactint® polymeric colorants, and Palmer® polymeric colorants, all of which are available from Milliken Chemical, a division of Milliken & Company of Spartanburg, SC. Liquitint® polymeric colorants are characterized in that they are water soluble, non-staining, colorants. They are widely used in laundry detergents, fabric softeners, and other consumer and industrial cleaning products. Liquitint® polymeric colorants are generally bright liquid colorants which, depending on the specific colorant, exhibit varying degrees of solubility in water. These colorants may also be characterized as being generally compatible with other chemicals present in their end-use formulations and are typically easy to handle. Liquitint® polymeric colorants may be used to provide color in both aqueous and solid systems. The unique polymeric nature of Liquitint® polymeric colorants provides reduced staining to skin, textiles, hard surfaces, equipment, and the like.

Reactint® polymeric colorants are liquid polymeric colorants useful for coloring polyurethane and other thermoset resins. These colorants are reactive polymeric colorants that consist of chromophores which are chemically bound to polyols. This arrangement allows the polymeric colorant to react into the polyurethane polymer matrix. Unlike pigment pastes, which are dispersions of solid particles in a liquid, Reactint® polymeric colorants are 100% homogeneous liquids that are soluble in polyol and will not settle over time. Because of this pure liquid and easy to disperse nature, it is possible to blend Reactint® colorants in-line and on-the-fly, while producing polyurethane foams and resins.

Palmer® polymer colorants are liquid colorants specially developed for use in washable applications, such as in markers, paints and other art products. They contain no heavy metals, are non-toxic, and have excellent non-staining properties on skin, fabric and other surfaces. Palmer® polymeric colorants have very good compatibility with aqueous ink formulations and provide bright colors.

In one aspect of the invention, the chromophore has a structure of:

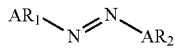

wherein $AR_1$ and $AR_2$ are independently selected from the group consisting of alkenyl groups, substituted alkenyl groups, aryl groups, substituted aryl groups, heteroaryl groups, and substituted heteroaryl groups; one of the $AR_1$ or $AR_2$ group can further substituted with another azo chromophore to form a bis azo. In one aspect, the substituted heteroaryl group is a substituted thiazolium group.

In another aspect of the invention, the chromophore has a structure of:

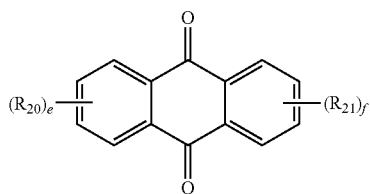

II wherein e and f are independently integers from 0 to 4; each $R_{20}$ and $R_{21}$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups.

In another aspect of the invention, the chromophore has a structure selected from:

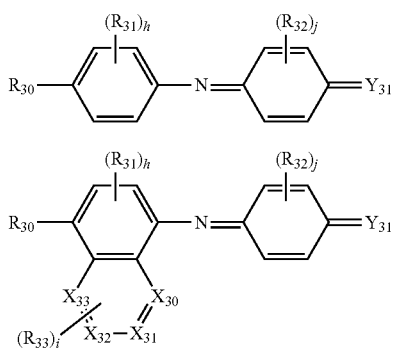

(III)

(IIIa)

wherein h, i, and j are independently integers from 0 to 4; provided in structure IIIa h is an integer from 0 to 2. $Y_{31}$ is selected from the group consisting of =O, =S, =NR$_{34}$, and =N$^+$R$_{34}$R$_{35}$; $R_{30}$ is selected from the group consisting of —O—, —S—, —OR$_{35}$ and —NR$_{36}$R$_{37}$. Each $R_{34}$, $R_{35}$, $R_{36}$ and $R_{37}$ is independently selected from the group consisting of hydrogen, alkyl groups, substituted alkyl groups, aryl groups, substituted aryl groups, heteroaryl group, substituted heteroaryl group, acyl groups, —C(O)OR$_5$, —C(O)R$_5$, and —C(O)NR$_5$R$_6$. each $R_{31}$, $R_{32}$ and $R_{33}$ group is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups. $X_{30}$, $X_{31}$, $X_{32}$, and $X_{33}$ are independently selected from the group consisting of a carbon atom and a nitrogen atom, provided no more than two of $X_{30}$, $X_{31}$, $X_{32}$, and $X_{33}$ are nitrogen atoms.

In another aspect of the invention, the chromophore has a structure of:

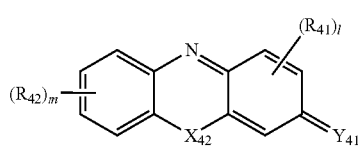

IV wherein $X_{42}$ is selected from the group consisting of an oxygen atom, a sulfur atom, SiR$_{45}$R$_{46}$, and NR$_{45}$. $Y_{41}$ is selected from the group consisting of =O, =S, =NR$_{46}$, and =N$^+$R$_{45}$R$_{46}$; $R_{45}$ and $R_{46}$ is selected from the group consisting of hydrogen, alkyl groups, substituted alkyl groups, aryl groups, substituted aryl groups, heteroaryl group, substituted heteroaryl group, —S(O)$_2$OH, —S(O)$_2$O$^-$[M$^+$], —C(O)OR$_5$, —C(O)R$_5$, and —C(O)NR$_5$R$_6$. l is an integer from 0 to 3 and m is an integer from 0 to 4. Each $R_{41}$ and $R_{42}$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —SR$_5$, —S(O)$_2$NR$_5$R$_6$, and —P(O)$_2$R$_5$; M is a cation; wherein at least one $R_{42}$ group is selected from the group consisting of —OR$_5$, —SR$_5$ and —NR$_5$R$_6$. $R_5$ and $R_6$ are independently selected from the group consisting of hydrogen, alkyl groups, substituted alkyl groups, aryl groups, and substituted aryl groups.

In another aspect of the invention, the chromophore has a structure of:

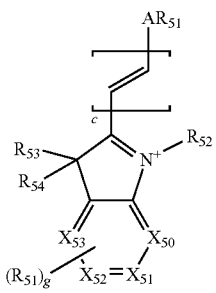

V wherein $AR_{51}$ is selected from the group consisting of alkenyl groups, substituted alkenyl groups, aryl groups, substituted aryl groups, heteroaryl groups, substituted heteroaryl groups; $R_{52}$ $R_{53}$ and $R_{54}$ are independently selected from the group consist of hydrogen and $R_{51}$. Each $R_{51}$ is independently selected from halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation, provided $R_{51}$ is not a hydrogen; $R_5$ and $R_6$ are independently selected from the group consisting of hydrogen, alkyl groups, substituted alkyl groups, aryl groups, and substituted aryl groups; c is an integer from 1 to 10. $X_{50}$, $X_{51}$, $X_{52}$, and $X_{53}$ are independently selected from the group consisting of a carbon atom and a nitrogen atom, provided no more than two of $X_{50}$, $X_{51}$, $X_{52}$, and $X_{53}$ are nitrogen atoms; g is an integer from 1 to 4; wherein the structure V can exist in an ionic form that accompanies its counter ion to maintain electric neutrality.

In another aspect of the invention, the chromophore has a structure of:

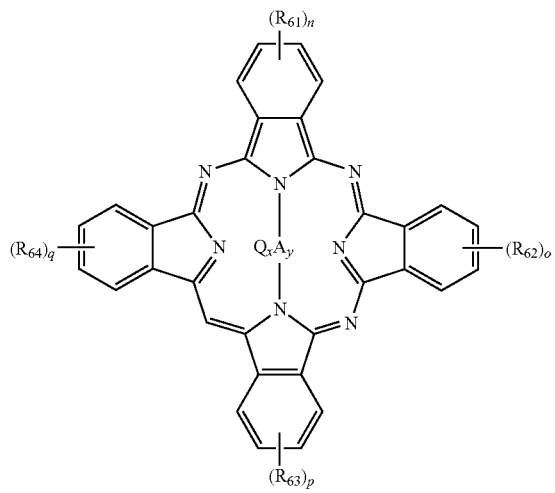

VI wherein each $R_{61}$, $R_{62}$, $R_{63}$, and $R_{64}$ group is independently selected halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4. $R_5$ and $R_6$ are independently selected from the group consisting of hydrogen, alkyl groups, substituted alkyl groups, aryl groups, and substituted aryl groups. Q is hydrogen, metal ion, or metalloids; A is the anion. x is a positive integer, and y is an integer including zero so that the divalent group -Q$_x$A$_y$- is neutral.

In another aspect of the invention, the chromophore has a structure of:

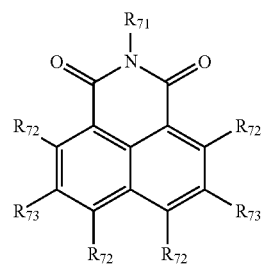

VII wherein each $R_{71}$, $R_{72}$ and $R_{73}$ group is independently selected hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)NR$_6$NR$_7$R$_8$, —NR$_5$C(O)SR$_5$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4. $R_5$, $R_6$, $R_7$ and $R_8$ are independently selected from the group consisting of hydrogen, alkyl groups, substituted alkyl groups, aryl groups, and substituted aryl groups, provided at least one $R_{72}$ groups is —OR$_5$ or —NR$_5$R$_6$ group.

In another aspect of the invention, the chromophore has a structure selected

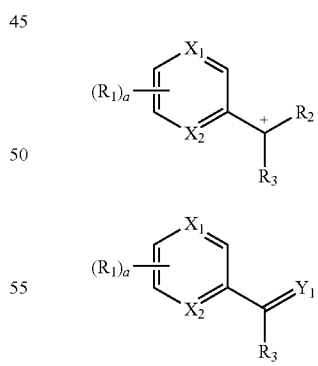

VIII

VIIIa wherein $X_1$ and $X_2$ are selected from the group consisting of a carbon atom and a nitrogen atom; a is an integer from 0 to 5, provided a is an integer from 0 to 4 when one of $X_1$ and $X_2$ is a nitrogen atom and a is an integer from 0 to 3 when both $X_1$ and $X_2$ are nitrogen atoms; each $R_1$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_5$, and —P(O)$_2$R$_5$; M is a cation; R$_5$ and R$_6$ are independently selected from the group consisting of hydrogen, alkyl groups, substituted alkyl groups, aryl groups, and substituted aryl groups; R$_2$ and R$_3$ is selected from the group consisting of alkenyl groups, substituted alkenyl groups, aryl groups, substituted aryl groups, heteroaryl groups, and substituted heteroaryl groups; Y$_1$ is selected from the group consisting of =O, =S, =NR$_5$, and =N$^+$R$_5$R$_6$; wherein the structure VIII and VIIIa can exist in an ionic form that accompanies its counter ion to maintain electric neutrality.

In another aspect of the invention, the chromophore has a structure of:

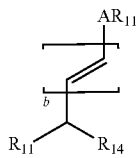

IX wherein AR$_{11}$ is selected from the group consisting of alkenyl groups, substituted alkenyl groups, aryl groups, substituted aryl groups, heteroaryl groups, and substituted heteroaryl groups; R$_{11}$ and R$_{14}$ are independently selected from the group consist of hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; R$_5$ and R$_6$ are independently selected from the group consisting of hydrogen, alkyl groups, substituted alkyl groups, aryl groups, and substituted aryl groups; b is an integer from 1 to 10.

In one aspect of the invention, the colorant has the following structure:

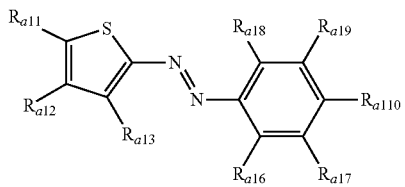

I-A wherein each R$_{a11}$ to R$_{a110}$ group is independently selected from the group consisting of hydrogen, deuterium and R$^v$; each R$^v$ is independently selected from the group consisting of halogens, nitro, nitrile, alkyl, substituted alkyl, alkenyl, substituted alkenyl, aryl, substituted aryl, alkynyl, substituted alkynyl, —(CH$_2$)$_n$—O—R$^x$, —(CH$_2$)$_n$—NR$^x$R$^y$, —C(O)R$^x$, —C(O)OR$^x$, —C(O)O—, —C(O)NR$^x$R$^y$, —OC(O)R$^x$, —OC(O)OR$^x$, —OC(O)NR$^x$R$^y$, —S(O)$_2$R$^x$, —S(O)$_2$OR$^x$, —S(O)$_2$O—, —S(O)$_2$NR$^x$R$^y$, —NR$^x$C(O)R$^y$, —NR$^x$C(O)OR$^y$, —NR$^x$C(O)SR$^y$, —NR$^x$C(O)NR$^y$R$^z$, —OR$^x$, —NR$^x$R$^y$, —P(O)$_2$R$^x$, —P(O)(OR$^x$)$_2$, —P(O)(OR$^x$)O—, and —P(O)(O$^-$)$_2$; wherein the index n is an integer from 0 to 4; and wherein R$^x$, R$^y$ and R$^z$ are independently selected from the group consisting of hydrogen, alkyl, substituted alkyl, alkenyl, substituted alkenyl, aryl, substituted aryl, alkynyl, substituted alkynyl, and R$^u$; R$^u$ is an organic group composed of one or more organic monomers with said monomer molecular weights ranging from 28 to 500. In another aspect of the invention, at least one of the R$_{a11}$, R$_{a12}$, and R$_{a13}$ is an electro-withdrawing group selected from halogens, nitro, nitrile, nitroso, —C(O)R$^x$, —C(O)OR$^y$, —C(O)NR$^x$R$^y$, —OC(O)R$^x$, —OC(O)OR$^x$, —OC(O)NR$^x$R$^y$, —S(O)$_2$R$^x$, —S(O)$_2$OR$^x$, —P(O)$_2$R$^x$, and —P(O)(OR$^x$)$_2$ groups. In yet a further aspect, the R$_{a11}$ and R$_{a13}$ groups are —CN groups, and R$_{a12}$ is a methyl group. In another aspect of the invention, R$_{a16}$, R$_{a17}$, R$_{a18}$, R$_{a19}$, R$_{a110}$ are independently selected from hydrogen, halogens, methyl group, ethyl groups, propyl groups, isopropyl group, n-butyl group, isobutyl groups, 2-butyl groups, tert-butyl groups, —(CH$_2$)$_n$O—R$^x$, —(CH$_2$)$_n$—NR$^x$R$^y$, —OR$^x$, and —NR$^x$R$^y$, and at least one of R$_{a16}$, R$_{a17}$, R$_{a18}$, R$_{a19}$, R$_{a110}$ is —OR$^x$, or —NR$^x$R$^y$. In a further aspect, two or more of R$_{a16}$, R$_{a17}$, R$_{a18}$, R$_{a19}$, R$_{a110}$ are connected to each other through covalent bonds to form a ring structure fused with the benzene ring in Formula I-A. In another aspect, the ring structure fused with the benzene ring in Formula I-A is one of naphthalene, tetrahydroquinoline, tetrahydroisoquinoline, indoline, and isoindoline. In another aspect, the ring structure is substituted by one or more R$_{a16}$ groups. In yet another aspect, two of R$^x$, R$^y$, or R$^z$ are attached to the same carbon or nitrogen group and form the ring structure. In a further aspect, the ring structure is one of piperazine, piperidine, and pyrrolidine. In another aspect, the ring structure is further substituted by one or more R$_{a16}$ groups.

In one aspect of the invention, the colorant is a thiophene azo colorant according to the following structure:

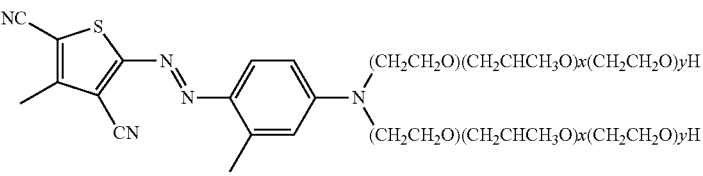

wherein each x and y are independently integers from 0 to 20.

It is also contemplated to be within the scope of the present invention that other colorants may be combined with the polymeric colorant to form the coloring agent portion of the hair care composition. For example, a colorant selected from one or more of the following classes may be suitable: acid dyes, basic dyes, direct dyes, solvent dyes, vat dyes, mordant dyes, indigoid dyes, reactive dyes, disperse dyes, sulfur dyes, fluorescent dyes; pigments, both organic and inorganic; natural colorants; and the like. Thus, the coloring agent of the hair care composition may be comprised of a blend or mixture of a polymeric colorant and a non-polymeric colorant. The polymeric colorant and the non-polymeric colorant may have the same chromophore groups, or they may have different chromophore groups.

The hair care composition of the present invention is prepared by combining at least one hair care ingredient with at least one polymeric colorant. The hair care composition thus formed may be a substantially homogenous mixture.

A method for preparing the hair care composition of the present invention is comprised of the following steps:
 (a) providing at least one hair care ingredient;
 (b) providing at least one polymeric colorant; and
 (c) combining the at least one hair care ingredient and the at least one polymeric colorant to form a polymeric colorant-containing hair care composition.

A method for applying color to hair according to the present invention is comprised of the following steps:
 (a) providing a polymeric colorant-containing hair care composition;
 (b) applying the polymeric colorant-containing hair care composition to hair;
 (c) allowing the polymeric colorant-containing hair care composition to contact the hair for a period of time; and
 (d) optionally, removing the polymeric colorant-containing hair care composition from the hair.

A method for bleaching and applying color to hair according to the present invention is comprised of the following steps:
 (a) providing a polymeric colorant-containing hair care composition, wherein the composition further comprises an oxidizing agent;
 (b) applying the composition to hair;
 (c) allowing the composition to contact the hair for a period of time; and
 (d) optionally, removing the composition from the hair.

The hair care composition may be allowed to contact the hair for a period of time in the range from 10 seconds to 1 hour, or in the range from 30 seconds to 45 minutes, or in the range from 1 minute to 30 minutes, or in the range from 3 minutes to 15 minutes. The hair may be wet with water prior to application of the hair care composition, or the hair may be dry when it is applied to the hair.

The hair care composition may be permanent (e.g. 80% of original color intensity is still visible after 20 wash cycles), semi-permanent (e.g. 80% of original color intensity is visible up to, but not subsequent to, 20 wash cycles), or temporary (e.g. 80% of original color intensity is visible up to, but not subsequent to, 5 wash cycles). The permanence of the hair color on the hair may depend on the specific polymeric colorant included in the composition and/or the amount of polymeric colorant included in the composition. For example, increasing the amount of polymeric colorant in the hair care composition may result in the color lasting longer on the hair. In contrast, including less polymeric colorant in the composition may result in the color lasting less time on the hair. Also, the amount of time the hair care composition remains in contact with the hair during the coloring process may affect amount of color, depth of color and/or shade, and the permanence of the hair color on the hair. For instance, leaving the composition on the hair for a longer period of time during the hair coloring process may result in a greater depth of shade and/or color and color that lasts longer on the hair.

In one aspect of the invention, the amount of polymeric colorant in the hair cream is in the range from 0.0001%-10%, or in the range from 0.1%-5%.

In one aspect of the invention, the molecular weight of polymeric colorant in the hair cream is in the range from 100-10000 Dalton or in the range from 200-5000 Dalton or in the range from 300 to 2000 Dalton.

At least one polymeric colorant as described herein may be added to a hair care composition for use in coloring hair. As a result, the invention also encompasses hair (or a keratin-containing material) containing at least one polymeric colorant. The invention further encompasses a process for bleaching and/or coloring hair (or a keratin-containing material) that includes the steps of providing hair, applying and/or depositing a hair care composition as described herein to the hair, allowing the composition to contact the hair for a period of time, and further agitating, rinsing, and/or drying the thus treated hair.

For application in non-oxidative systems, there is typically a single component which is often a cream (but not limited to such) which contains hair care ingredients listed previously and the color mixed together. The single component cream is put on the hair and the color deposits directly on the hair. The colored cream is then washed off, leaving colorant on the hair.

For application in oxidative systems, there are typically two components. One component contains an oxidative species (such as hydrogen peroxide). The second component contains other species, typically designed to raise pH, but could also contain other oxidative species such as persulfates. In one aspect of the invention, the two components are mixed together before applying to hair. The initial application includes the polymeric colorant in the hydrogen peroxide cream, not in the second component. However, it is conceivable to put the polymeric colorant in the second component instead.

Thus, in one embodiment, at least one polymeric colorant is mixed into an oxidizer containing cream. Immediately before use, the polymeric colorant/hydrogen peroxide containing cream is mixed with at least one other component that raises the pH a sufficient amount to activate the hydrogen peroxide. In an alternative embodiment, the polymeric colorant may be added to the second component. In this instance, the second component is added to the uncolored hydrogen peroxide cream immediately before use.

While the invention described herein has been directed mainly to hair care compositions containing polymeric colorants, it is not limited to only those compositions. The composition may contain a combination of polymeric colorant and another coloring agent. Other coloring agents include, for example, dyes, pigments, and combinations thereof.

Suitable dyes include small molecule dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. Examples of small molecule dyes include those selected from the group consisting of Colour Index (Society of Dyers and Colourists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159, small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In one aspect of the invention, the components of the hair care composition may be prepared by combining the components in any convenient order and by mixing, e.g., agitating, the resulting component combination to form a phase stable semi-liquid (i.e. cream) composition. In another process for preparing such compositions, a liquid matrix is formed containing at least a major proportion, and preferably substantially all, of the liquid components, with the liquid components being thoroughly admixed by imparting shear agitation to this liquid combination. For example, rapid stirring with a mechanical stirrer may usefully be employed. While shear agitation is maintained, substantially all of any solid form ingredients can be added. Agitation of the mixture is continued, and if necessary, can be increased at this point to form a solution or a uniform dispersion of insoluble solid phase particulates within the liquid phase. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The hair care composition of the present invention may be combined with other molecules, compounds, and/or agents useful for applying the composition to hair and/or for enhancing color performance. Other molecules, compounds and/or agents include, for example, surfactants, solvents, preservatives, antimicrobial agents, antibacterial agents, perfumes, and the like, and combinations thereof.

The hair care compositions of the present invention may also include any number of additional optional ingredients. These include conventional hair colorant composition components such as emollient oils, surfactants which may include nonionic, anionic, cationic, zwitterionic, betaine surfactants, polar solvents, chelating agents, pH adjusters, conditioning agents, and other ingredients. The various optional hair cream composition ingredients, if present in the compositions herein, should be utilized at concentrations conventionally employed to bring about their desired contribution to the composition and/or coloring process. Frequently, the total amount of such optional hair cream composition ingredients can range from about 0.01% to about 50%, more preferably from about 0.1% to about 30%, by weight of the composition.

EXAMPLES

The following polymeric colorants were made and evaluated in a variety of different hair care compositions:

TABLE 1

Polymeric colorants made and evaluated.

| Example # | Structure | Color |
| --- | --- | --- |
| Example 1 | 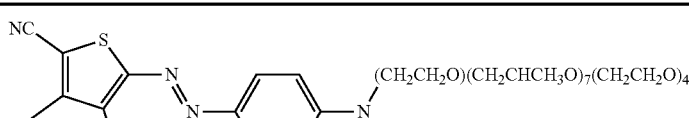 | Violet |
| Example 2 | 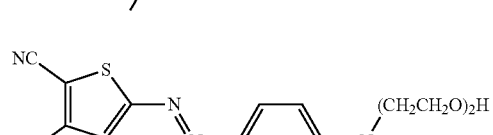 | Violet |

TABLE 1-continued

Polymeric colorants made and evaluated.

| Example # | Structure | Color |
|---|---|---|
| Example 3 | Thiophene (with NC, CH₃, CN substituents)–N=N–phenyl (with OCH₃, OCH₃, and N((CH₂CH₂O)₂H)((CH₂CH₂O)₃H)) | Violet |
| Example 4 | Thiophene (with NC, CH₃, CN substituents)–N=N–tetrahydroquinoline with N-(CH₂CH₂O)₅H | Violet |
| Example 5 | Thiophene (with NC, CH₃, CN substituents)–N=N–phenyl (with CH₃ and N((CH₂CH₂O)(CH₂CHCH₃O)₉H)((CH₂CH₂O)(CH₂CHCH₃O)₈H)) | Violet |
| Example 6 | Triarylmethyl cation: H(OCH₂CH₂)₃–N((CH₂CH₂O)₂H)–C₆H₄–C⁺(–C₆H₄–N((CH₂CH₂O)₂)((CH₂CH₂O)₃H))–C₆H₄–SO₃⁻ | Blue |
| Example 7 | Triarylmethyl cation: H(OCH₂CH₂)₁₀–N((CH₂CH₂O)₁₀H)–C₆H₄–C⁺(–C₆H₄–N((CH₂CH₂O)₁₀H)((CH₂CH₂O)₁₀H))–C₆H₄–SO₃⁻ | Blue |
| Example 8 | Bis(tetrahydroquinoline) methyl cation, each N-(CH₂CH₂O)₁₀H, central C⁺ bonded to phenyl with 2,4-(SO₃⁻)₂ | Green |

TABLE 1-continued
Polymeric colorants made and evaluated.
| Example # | Structure | Color |
|---|---|---|
| Example 9 | 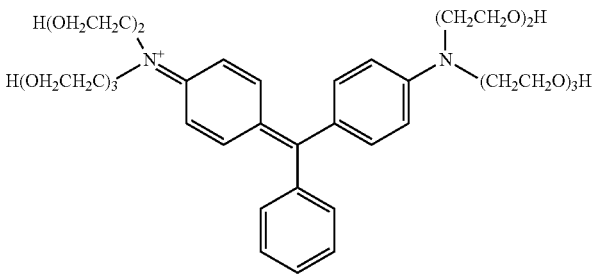 | Green |
| Example 10 | 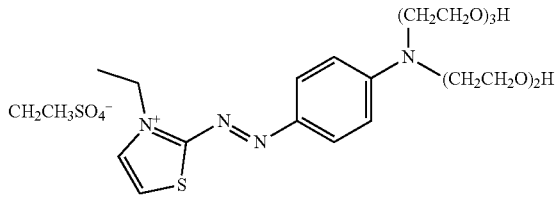 | Blue |
| Example 11 | 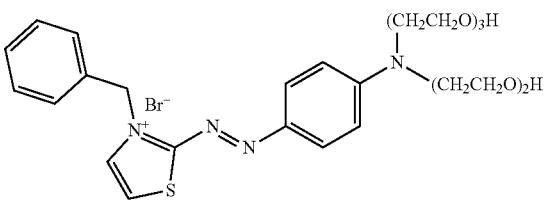 | Blue |
| Example 12 | 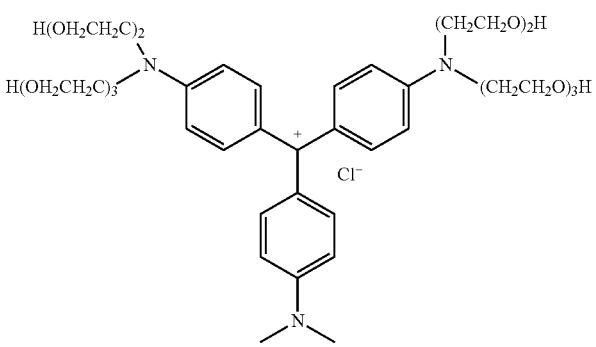 | Violet |
| Example 13 | 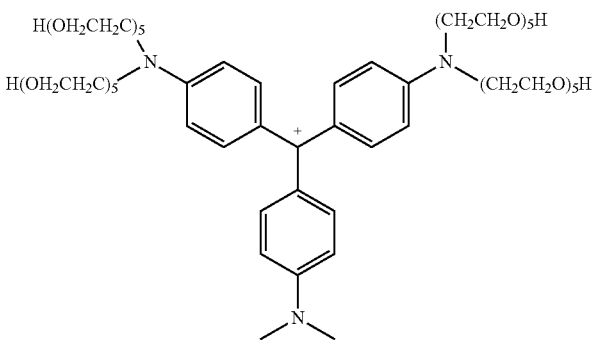 | Violet |

TABLE 1-continued

Polymeric colorants made and evaluated.

| Example # | Structure | Color |
|---|---|---|
| Example 14 | [triphenylmethane cation structure with N-substituents: H(OH₃CHCH₂C)₂(OH₂CH₂C)₂ and H(OH₃CHCH₂C)₃(OH₂CH₂C)₃ on one aniline N; (CH₂CH₂O)₂(CH₂CHCH₃O)₂H and (CH₂CH₂O)₃(CH₂CHCH₃O)₃H on second aniline N; N(CH₃)₂ on third phenyl; Cl⁻ counterion] | Violet |
| Example 15 | [triphenylmethane cation with 2-methyl substituted aniline rings; N-substituents H(OH₂CH₂C)₂ and H(OH₂CH₂C)₃; (CH₂CH₂O)₂H and (CH₂CH₂O)₃H; third ring N(CH₃)₂; Cl⁻] | Blue |
| Example 16 | [thiazol-2-yl-azo-phenyl-N((CH₂CH₂O)₃H)((CH₂CH₂O)₂H)] | Red |
| Example 17 | [4-methylbenzothiazol-2-yl-azo-(3-methylphenyl)-N((CH₂CH₂O)(CH₂CHCH₃O)₅(CH₂CH₂O)₃H)₂] | Red |
| Example 18 | [4-methylbenzothiazol-2-yl-azo-(3-methylphenyl)-N((CH₂CH₂O)₁₀H)₂] | Red |
| Example 19 | [4-methylbenzothiazol-2-yl-azo-(3-methylphenyl)-N((CH₂CH₂O)₅H)₂] | Red |

TABLE 1-continued

Polymeric colorants made and evaluated.

| Example # | Structure | Color |
|---|---|---|
| Example 20 | 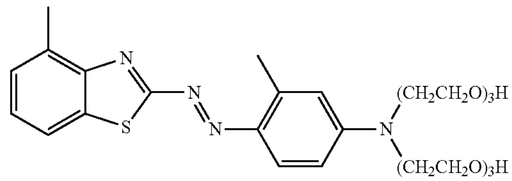 | Red |
| Example 21 | 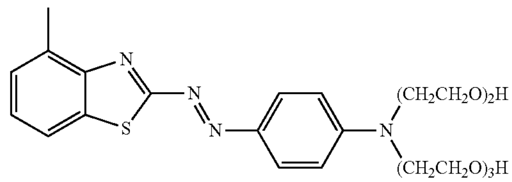 | Red |
| Example 22 | 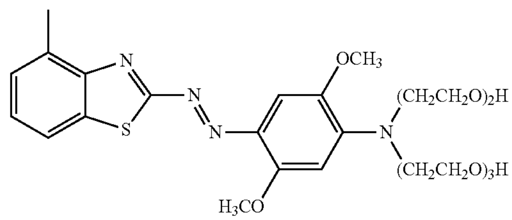 | Red |
| Example 23 | 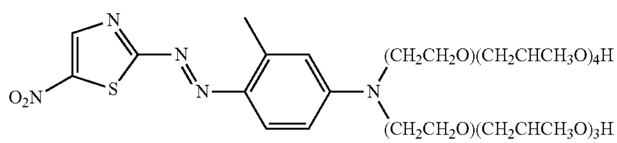 | Blue |
| Example 24 | 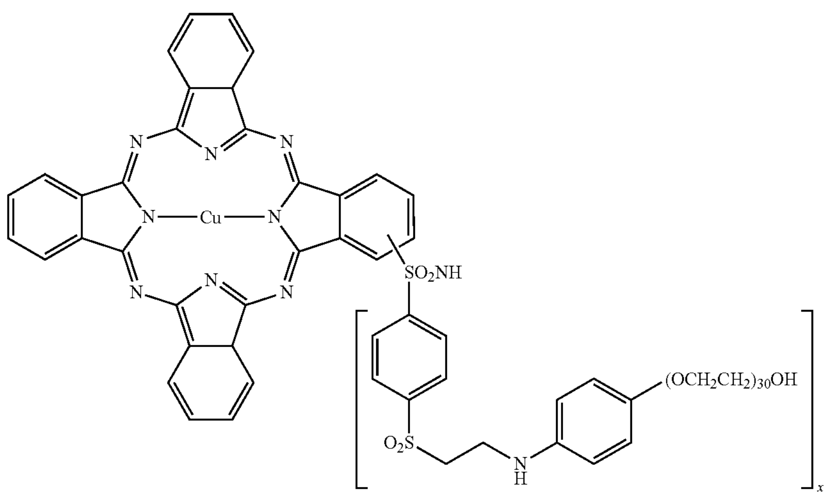 | Blue |
| Example 25 | 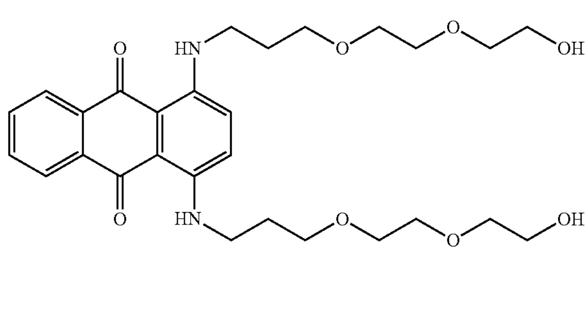 [SMILES: O=C1c2ccccc2C(=O)c2c(NCCCOCCOCCO)ccc(NCCCOCCOCCO)c21] | Blue |

TABLE 1-continued

Polymeric colorants made and evaluated.

| Example # | Structure | Color |
|---|---|---|
| Example 26 | 1,4-bis[(3-(2-(2-(2-(poly(caprolactone))oxy)ethoxy)ethoxy)propyl)amino]anthracene-9,10-dione with terminal —(COCH$_2$CH$_2$CH$_2$CH$_2$CH$_2$O)H chains | Blue |
| Example 27 | 1,3,3-trimethyl-2-[2-[4-[N,N-bis((CH$_2$CH$_2$O)$_{10}$COCH$_3$)amino]-2-methylphenyl]ethenyl]-3H-indolium acetate (CH$_3$COO$^-$) | Red |
| Example 28 | 1,3,3-trimethyl-2-[2-[4-[N,N-bis((CH$_2$CH$_2$O)$_{5}$COCH$_3$)amino]-2-methylphenyl]ethenyl]-3H-indolium acetate (CH$_3$COO$^-$) | Red |
| Example 29 | 1,3,3-trimethyl-2-[2-[4-[N,N-bis((CH$_2$CH$_2$O)$_{3}$COCH$_3$)amino]-2-methylphenyl]ethenyl]-3H-indolium acetate (CH$_3$COO$^-$) | Red |
| Example 30 | 1,3,3-trimethyl-2-[2-[4-[N-((CH$_2$CH$_2$O)$_{2}$COCH$_3$)-N-((CH$_2$CH$_2$O)$_{3}$COCH$_3$)amino]phenyl]ethenyl]-3H-indolium acetate (CH$_3$COO$^-$) | Red |
| Example 31 | 3-[(4-[N-((CH$_2$CH$_2$O)$_2$H)-N-((CH$_2$CH$_2$O)$_3$H)amino]phenyl)azo]benzenesulfonate sodium salt (NaO$_3$S) | Yellow |
| Example 32 | 4-[[4-[N,N-bis((CH$_2$CH$_2$O)$_5$H)amino]-2-methylphenyl]azo]-N,N-bis(2-hydroxyethyl)benzenesulfonamide | Yellow |

TABLE 1-continued
Polymeric colorants made and evaluated.
| Example # | Structure | Color |
|---|---|---|
| Example 33 | 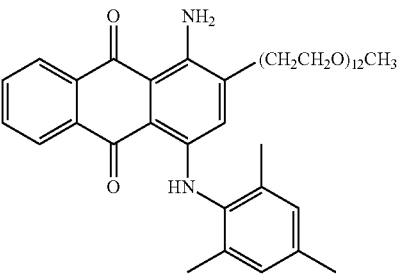 | Violet |
| Example 34 | 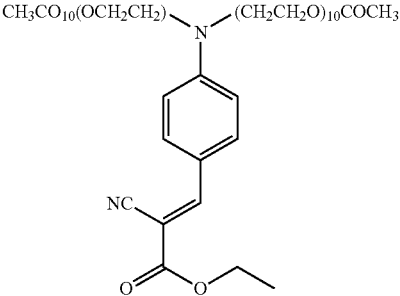 | Yellow |
| Example 35 | 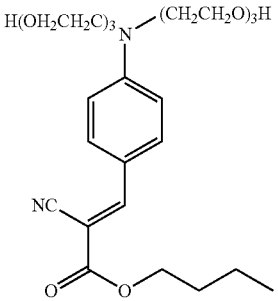 | Yellow |
| Example 36 | 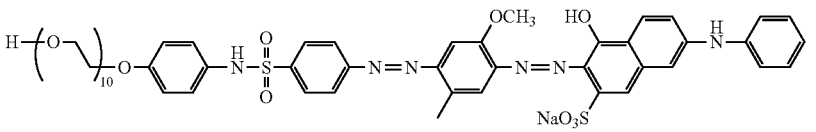 | Violet |
| Example 37 | 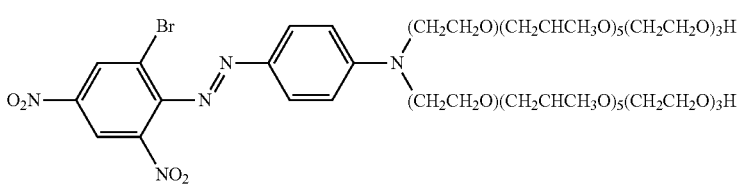 | Violet |

All the above colorants are able to render color to hair as demonstrated in various Application examples below. As these materials are polymeric, there exists a distribution around the mean number of repeat units; for the materials listed in the table above, the mean value of repeat units is listed.

To prepare the hair care composition containing a polymeric colorant, the polymeric colorant may be mixed with the hair color or the colorant may be added to an already made hair care composition. For example, the following hair care composition according to the invention can be prepared:

Hair Cream Formulations 1 to 3

TABLE 2

Examples of Hair Cream Formulations

| Ingredients | Formulation 1 | Formulation 2 | Formulation 3 |
|---|---|---|---|
| Water | Add to 100 | Add to 100 | Add to 100 |
| Ethoxydiglycol | 5.0 | 5.0 | 5.0 |
| Methylparaben | 0.20 | 0.20 | 0.20 |
| Disodium EDTA | 0.05 | 0.05 | 0.05 |
| Aminomethyl propanol | 3.60 | 3.60 | 0 |
| Monoethanolamine | 0 | 0 | 3.60 |
| Erythorbic acid | 0.06 | 0.06 | 0.06 |
| Example 1 | 1 | | |
| Example 10 | | 1 | |
| Example 15 | | | 1 |
| Veegum | 1.00 | 0.50 | 1.00 |
| Oleic acid | 9.38 | 9.38 | 9.38 |
| Cetearyl alcohol | 3.00 | 3.00 | 3.00 |
| Polawax | 1.50 | 1.50 | 1.50 |
| Oleth-20 | 0.75 | 0.75 | 0.75 |
| Steareth-21 | 0.53 | 0.53 | 0.53 |
| Oleyl alcohol | 0.30 | 0.30 | 0.30 |
| Fragrance | 0.50 | 0.50 | 0.50 |

The hair care compositions can be prepared by placing water in a beaker having a homogenizer mill attached and heating to 70-75° C. The homogenizer mill is then turned on and the veegum sprinkled into the beaker. The mixture is milled for 15 minutes. While maintaining the temperature, ethoxy diglycol, disodium EDTA, erythorbic acid and methylparaben are added to the mixture, which is further milled for about 15 minutes. In a separate beaker the aminomethyl propanol, monoethanolamine, and water are combined, then this mixture is added to the mixture of other ingredients. The batch is transferred to a turbine/sweep kettle.

Separately, the oil ingredients—oleic acid, cetearyl alcohol, emulsifying wax, oleth-20, oleyl alcohol, and Steareth 21—are combined and heated to 70-75° C. The oil phase is then combined with the other ingredients and mixed well while maintaining the temperature at 70-75° C. The batch was cooled to 35-40° C. The fragrance oil and color are added, and the composition is mixed for an additional 15 minutes. The batch is cooled to 25° C.

Alternatively, hair care compositions according to the invention can prepared by mixing the above polymeric colorant examples with commercially available hair care compositions. These hair care compositions may include semi-permanent hair coloring cream. Such examples may include Igora ColorWorx Dilutor (Schwarzkopf), Colorista Clear Mixer (L'Oreal), Color Charm Paints Clear (Wella), and Color Fresh Create Tomorrow Clear (Wella). These hair care compositions may also include shampoo. Such examples may include After Color Treatment Shampoo (Fanola), Tresemme Pro Pure Micellar Moisture Shampoo (Unilever), Pantene Nutrient Blends Illuminating Color Care Shampoo (P&G), BC Bonacure pH 4.5 Color Freeze Micellar Rich Shampoo (Schwarzkopf), Free & Clear Shampoo for Sensitive Skin (Pharmaceutical Specialties, Inc.), EverPure Blonde Shampoo (L'Oreal), and Schauma 7 Herbs Shampoo (Schwarzkopf). These hair care compositions may also include conditioner, deep conditioner, and conditioning masks. Such examples may include EverPure Blonde Conditioner (L'Oreal), Pantene Nutrient Blends Illuminating Color Care Conditioner (P&G), Pantene Pro-V Classic Clean Conditioner (P&G), Nutri Care Restructuring Conditioner (Fanola), Schauma 7 Herbs Conditioner (Schwarzkopf). These hair care compositions may also include a variety of leave-in products such as leave-in conditioner, hair spray, mousse, gel, wax, etc.

Polymeric colorants were also evaluated by the following procedure: Polymeric colorants were added to hair care compositions. Each sample was mixed using a SpeedMixer at 1500 rpm until a visually uniform mixture was obtained (SpeedMixer Inc., Landrum, SC). The colored hair care composition was transferred to a large weigh boat with the hair sample. A specific amount of the mixture was spread all over the hair and worked into the hair with fingertips until the mixture was fully incorporated evenly throughout the hair. The amount varied based on the type of hair care composition and is specified in each example. The colored hair care composition was allowed to sit on the hair for a specific amount of time and then the hair sample was rinsed thoroughly with lukewarm water, combed, and dried in the oven at 60° C. for 45 minutes. The amount of time varied based on the type of hair care composition and is specified in each example. The color of hair was measured using the X-Rite Color i7 with a 6 mm aperture. The result of each measurement was an L*, a*, b* value with a D-65, 10° observer basis. The hair was twisted tight and pressed to the aperture while taking the measurement. An average of 6-8 measurements was used. The primary means of comparing samples or evaluating the amount of color deposited onto the hair was ΔE which was calculated as described below and Yellowness Index (YI) which was calculated per ASTM Method E313.

Method for Calculating ΔE:

ΔE was used to indicate the efficiency of the polymeric colorant when dyeing hair. L*, a*, b* values were taken from the hair before coloring and after coloring. The changes in L*, a*, b*, ΔL*, Δa*, Δb*, were calculated and converted into ΔE values by the following equation:

$$\Delta E = \sqrt{\Delta L^{*2} + \Delta a^{*2} + \Delta b^{*2}}$$

The higher ΔE values means greater hair color change before and after dyeing, and thus, more efficient hair colorants.

Application Example 1

Polymeric colorants of this invention were evaluated as semi-permanent hair colorants by coloring blonde hair swatches (bleached blonde from dark black). The blonde human hair swatches are commonly used to evaluate coloration by stylists and can be obtained from many different retailers. The hair care composition in this example was an uncolored semi-permanent hair coloring cream, Igora ColorWorx Dilutor (Schwarzkopf). For each colorant, the amount of color in the cream was adjusted so that each sample exhibited the same color strength, meaning the amount of chromophore or absorbance in each cream was the same despite the different polymer chain lengths. The maximum absorbance of the colored cream was 0.1 when measured with 1 cm path length at concentration of 1 grams/liter in methanol. The amount of cream used was 1 gram of cream per gram of hair. The cream was contacted with the hair 20 minutes before rinsing off. To evaluate the amount of color deposited onto the yak hair, the ΔE value for the colored vs. the uncolored hair was used. The results are shown in Table 3. Example compounds from Table 1 not evaluated in Table 3 are evaluated in other tests.

TABLE 3

Colorant Deposition from Semi-Permanent Hair Coloring Cream onto Bleached Hair

| Colorant | ΔE Deposition |
|---|---|
| Example 1 | 12.2 |
| Example 2 | 25.9 |
| Example 3 | 35.8 |
| Example 4 | 26.2 |
| Example 6 | 38.0 |
| Example 7 | 26.3 |
| Example 8 | 13.8 |
| Example 9 | 44.2 |
| Example 10 | 63.7 |
| Example 11 | 63.6 |
| Example 12 | 66.7 |
| Example 13 | 56.1 |
| Example 14 | 51.9 |
| Example 15 | 64.7 |
| Example 16 | 51.6 |
| Example 17 | 19.6 |
| Example 18 | 34.5 |
| Example 20 | 49.0 |
| Example 23 | 25.8 |
| Example 24 | 10.6 |
| Example 25 | 39.0 |
| Example 26 | 32.7 |
| Example 27 | 60.8 |
| Example 28 | 61.1 |
| Example 29 | 73.5 |
| Example 31 | 25.8 |
| Example 32 | 32.7 |
| Example 33 | 20.5 |
| Example 34 | 19.1 |
| Example 35 | 31.2 |
| Example 36 | 21.5 |

Application Example 2

From Table 3, the length of the polymer chains appears to affect deposition on the bleached hair (as example, compare Example 6 vs. 7, 12 vs. 13, 18 vs. 20, 28 vs. 29). The shorter polymer length tends to provide higher deposition. To further study this effect on a different substrate from bleached hair, three different colorants with the same chromophore but with different polymer lengths were tested on yak belly hair. The hair care composition in this example was an uncolored semi-permanent hair coloring cream, Igora ColorWorx Dilutor (Schwarzkopf). The amount of color in the cream was adjusted so that each sample exhibited the same color strength, meaning the amount of chromophore or absorbance in each cream was the same despite the different polymer chain lengths. Similar to Application Example 1, the maximum absorbance of the colored cream was 0.1 when measured with 1 cm path length at concentration of 1 grams/liter in methanol. For this study, yak belly hair was used as the hair substrate and the hair was colored using the procedure above. The amount of cream used was 2 grams of cream per gram of hair. The cream was contacted with the hair 20 minutes before rinsing off. To evaluate the amount of color deposited onto the yak hair, the ΔE value for the colored vs. the uncolored hair was used. The results are shown in Table 4. The amount of color deposited decreases as the polymer chain length increases. As the number of EO units increase, the amount of deposition tends to decrease. The results indicate that 5 to 6 EO units is optimal.

TABLE 4

Colorant Deposition from Semi-Permanent Hair Coloring Cream onto Yak Hair

| Colorant | Average # of EO Units | ΔE Deposition |
|---|---|---|
| Example 30 | 5 | 48.8 |
| Example 28 | 10 | 32.4 |
| Example 27 | 20 | 13.5 |

Application Example 3

Polymeric colorants of this invention were compared to current commercial hair dyes by coloring blonde hair (bleached blonde from dark black). A red colorant (Example 16) was put into Igora ColorWorx diluter cream at 1.5 wt % and compared to current commercial product Igora ColorWorx Red cream which contained the dyes 4-hydroxypropylamino-3-nitrophenol and 3-nitro-p-hydroxyethylaminophenol. A yellow colorant (Example 35) was similarly put into Igora ColorWorx diluter cream at 1.5 wt % and compared to current commercial product Igora ColorWorx Yellow cream which contained the dyes HC Yellow No. 13 and HC Yellow No. 2.

Each colored cream was deposited onto hair as outlined above. The amount of cream used was 2 grams of cream per gram of hair. The cream was contacted with the hair 20 minutes before rinsing off. The L*a*b* color of the hair was then measured as outlined above. The hair was then washed using Schauma 7 Herbs Shampoo (Schwarzkopf) and dried with a hair dryer using the procedure below. The hair was fully wet using 40° C. tap water. Shampoo (0.2 grams of shampoo per 1 gram of hair) was then added to the hair and worked in using fingers for 30 seconds. The hair and shampoo were allowed to sit in a dish for another 30 seconds and then rinsed for 30 seconds using 40° C. tap water. The hair sample was then dried using a hair dryer. The hair was washed and dried twice and then its L*a*b* color was measured. The hair was then washed and dried two more times and measured again. To evaluate the amount of color deposited onto the hair and the amount of color retained on the hair after each sequence of washes, the ΔE value for the colored at any particular wash state vs. the uncolored hair was used. The retained hair color after two and four washes was evaluated by dividing the ΔE value of the washed hair by the ΔE value of the unwashed, initially deposited hair color. Higher values indicated better retention of hair color during the wash, with a value of 100% meaning no color loss.

The polymeric colorants demonstrated superior wash performance compared to the comparative dyes (Igora Red and Igora Yellow). Red polymeric colorant exhibited substantially more color remaining than Igora Red after four washes. The absolute ΔE number of the polymeric colorant was nearly double that of the dye product, and the retained color was nearly 85% compared to only 48% for the dye. The yellow polymeric colorant exhibited an even larger improvement over the yellow dye product. The retained color for the yellow polymeric colorant was 78% compared to only 37% for the yellow dye.

TABLE 5

Evaluation of Color Wash-Off Performance on Bleached Hair

| Metric | Igora Red | Red Polymeric Colorant (Ex. 16) | Igora Yellow | Yellow Polymeric Colorant (Ex. 35) |
|---|---|---|---|---|
| ΔE Initial Deposit | 55.6 | 61.7 | 40.7 | 47.7 |
| ΔE 2 washes | 41.5 | 58.6 | 24.5 | 44.1 |
| ΔE 4 washes | 26.9 | 52.1 | 14.9 | 37.4 |
| ΔE 2w/ΔE initial | 74% | 95% | 60% | 93% |
| ΔE 4w/ΔE initial | 48% | 85% | 37% | 78% |

This behavior exemplified in Table 5 is unexpected as the test results illustrate that reducing the size of the polymer increases deposition; as such, one might expect that the dye which had effectively zero polymer length would be superior to a polymeric colorant. However, it is believed, while not being bound to theory, that the polymeric colorants exhibited better wash performance compared to the dyes because the polymers prevent any aggregation of the colorants, which is a very common occurrence in dyes (especially in a generally oleophilic cream as is commonly used for hair coloring). Since the polymeric colorants are not aggregated and fully dispersed into the cream, it is believed they can more uniformly coat the hair fiber than the dyes which have a strong possibility of aggregation. This more uniformly coated hair fiber demonstrated less loss of color during washing compared to the dyes because the aggregated dyes are less uniformly coating the hair fiber.

Application Example 4

Polymeric colorants, like conventional hair dyes, can be used widely in a variety of different hair coloring formulations. This was demonstrated by taking a single polymeric colorant (Example 10) and mixing it into several different commercial uncolored semi-permanent hair coloring creams at 0.16% by mass and applied to bleached blonde hair. The amount of cream used was 1 grams of cream per gram of hair. The cream was contacted with the hair 20 minutes before rinsing off. The amount of color deposited onto the hair was evaluated by measure ΔE of the colored hair relative to the uncolored hair and is shown in Table 6.

There were four different creams evaluated, each with different ingredients in the creams. Igora ColorWorx Dilutor (Schwarzkopf) contained Aqua, Cetearyl Alcohol, PEG-8-Coconut Alcohol, Ceteareth-20, Disodium Cocoamphodipropionate, Methylparaben, Xanthan Gum, Sulfuric Acid, Sodium Silicate, Propylparaben-Etidronic Acid, Ethanolamine. Colorista Clear Mixer (L'Oreal) contained Aqua, Cetearyl Alcohol, Behentrimonium Chloride, Amodimethicone, Cetyl Alcohol, C12-15 Alkyl Benzoate, Isopropyl Alcohol, Hydroxyethyl-Cellulose, Trideceth-6, Guar Hydroxypropyltrimonium Chloride, Chlorhexidine Digluconate, Stearyl Alcohol, Myristyl Alcohol, Citric Acid, Cetrimonium Chloride, 2-Oleamido-1,3-Octadecanediol, Fumaric Acid, Sodium Hydroxide. Color Charm Paints Clear (Wella) contained Aqua, Cetearyl Alcohol, Propylene Glycol, Steareth-20, Phenoxyethanol, Parfum/Fragrance, Potassium Phosphate, Hexyl Cinnamal, Sodium Hydroxide, Citric Acid. Color Fresh Create Tomorrow Clear (Wella) contains Aqua, Cetearyl Alcohol, Propylene Glycol, Steareth-20, Phenoxyethanol, Mica, Potassium Phosphate, Titanium Dioxide/C177891, Sodium Hydroxide, Citric Acid. The polymeric colorant is highly effective in all the evaluated creams which demonstrates these materials will work in a wide range of different formulations, each with a wide variety of ingredients.

TABLE 6

Deposition Performance of a Polymeric Colorant (Example 10) in Different Semi-Permanent Hair Coloring Formulations

| Semi-Permanent Hair Coloring Cream | ΔE Deposition |
|---|---|
| Igora ColorWorx Dilutor (Schwarzkopf) | 67.4 |
| Colorista Clear Mixer (L'Oreal) | 68.9 |
| Color Charm Paints Clear (Wella) | 67.6 |
| Color Fresh Create Tomorrow Clear (Wella) | 66.8 |

Application Example 5

While hair coloring is often done using particularly designed hair coloring creams, it is also desirable to color or tone hair using other hair care compositions. Shampoo is a commonly used hair care composition that can also be used to deposit color onto hair. A range of polymeric colorants can be used to color hair in a shampoo formulation. The hair care composition in this example was a shampoo, BC Bonacure pH 4.5 Color Freeze Micellar Rich Shampoo (Schwarzkopf). For each colorant, the amount of colorant in the shampoo was adjusted so that each sample exhibited the same color strength, meaning the amount of chromophore or absorbance in each shampoo was the same despite the different polymer chain lengths and chromophore types. The maximum absorbance of the colored shampoo was 0.25 when measured with 1 cm path length at concentration of 1 grams/liter in methanol. For this study, bleached blonde hair was used as the hair substrate and the hair was colored using the procedure above. The amount of shampoo used was 0.2 grams of shampoo per gram of hair. The shampoo was contacted with the hair 3 minutes before rinsing off. To evaluate the amount of color deposited onto the hair, the ΔE value for the post shampoo vs. the pre-shampoo hair was used.

In addition, the Yellowness Index (YI) was calculated for the post shampoo and the pre-shampoo hair samples and the change in YI (ΔYI) from shampoo treatment calculated. When dark hair is bleached there is preferential destruction of certain melanin pigments which leads to an undesirable warm orange/yellow or "brassy" tone to the bleached hair. A major application of the dyes in shampoo is to neutralize this warm tone to a cooler or more white tone. By evaluating the ΔYI of the hair, one can observe the desired effect of toning or neutralizing the undesired warm tone. The more the YI decreases, the less yellow or brassy the hair appears; in other words, the more negative the ΔYI of the shampoo treatment, the better the colorant covers the undesired yellow tone.

In addition to the polymeric colorants evaluated for shampoo, a commercial dye commonly used in shampoo was also included as a comparative sample. External D&C Violet 2 (also known as Acid Violet 43) was formulated identically to the polymeric colorants in terms of absorbance per gram of shampoo. Additional mixing and time was required to fully disperse the powdered dye into the shampoo. Results are shown in Table 7. The polymeric colorants show a range of deposition performance as judged by ΔE. Unexpectedly, some of the polymeric colorants show greater deposition onto the hair in shampoo than the commonly used dye, Ext. D&C Violet 2. When the shade of the polymeric colorant is appropriate to neutralize the yellow tones of the hair (such as Example 10 and Example 11), the ΔYI is more strongly negative than comparative dye, implying that they are more effective at neutralizing yellow tones. Some colorants are not the desired shade to neutralize yellow tones in bleached hair, such as Example 30, but can be used for other colorations such as yellow, red, pink, etc.

TABLE 7

Deposition Performance in Shampoo for Different Colorants

| Colorant | ΔE | ΔYI |
|---|---|---|
| Comparative Example Ext. D&C Violet 2 | 7.0 | −12.0 |
| Example 10 | 17.7 | −29.5 |
| Example 11 | 11.6 | −21.1 |
| Example 30 | 7.5 | 2.3 |
| Example 2 | 7.0 | −11.0 |
| Example 4 | 5.4 | −7.6 |
| Example 12 | 4.7 | −8.3 |
| Example 22 | 3.6 | −1.4 |
| Example 26 | 2.7 | −5.5 |
| Example 5 | 2.4 | −3.3 |
| Example 1 | 1.3 | −1.2 |

Application Example 6

It is known that for toning of bleached hair with dye containing shampoo that the shampoo cannot be used daily because the dye has a tendency to continue to deposit or build over each wash cycle. Thus, the hair will go from yellow to desirably toned to undesirably violet or blue as the colorant continues to build. Because of the different physical properties of polymeric colorants compared to dyes, they can show better leveling behavior where they build to a certain level depending on loading and then stop building. This would allow one to safely use a shampoo daily and obtain the desired level of toning without the undesirable over-toning or violet/blue shading of hair. A polymeric colorant (Example 10) was formulated into shampoo and hair was repeatedly washed and dried over multiple cycles. A comparative example shampoo was made using Ext. D&C Violet 2 and the same experiment carried out with it.

For this example, the shampoo was BC Bonacure pH 4.5 Color Freeze Micellar Rich Shampoo (Schwarzkopf). For each colorant/dye, the amount of colorant in the shampoo was adjusted so that each sample exhibited the same color strength; the maximum absorbance of the colored shampoo was 0.043 when measured with 1 cm path length at concentration of 1 grams/liter in methanol. This is a colorant loading level similar to many commercial toning shampoos. Bleached blonde hair was used as the hair substrate. The amount of shampoo used was 0.2 grams of shampoo per gram of hair. The shampoo was contacted with the hair 3 minutes before rinsing off. To evaluate the amount of color deposited onto the hair in each wash, the ΔE value for the hair after vs. before each shampoo wash was used. Results are shown in Table 8. As before, the polymeric colorant deposits more in the first wash than the dye. Both the dye and polymeric colorant show lower deposition in the second and third wash then the first wash. Surprisingly, the polymeric colorant shows ever decreasing deposition with increasing washes past the third wash which indicates leveling while the dye shows a steady amount of deposition past the third wash which indicates continued building of the dye onto the hair. The polymeric colorant in this case shows a desirable behavior: strong initial deposition followed by rapid leveling. This would allow a consumer to observe a clear effect after only one or two washes but safely continue using the shampoo with reduced concern of over-toning or undesirably violet or blue coloring.

TABLE 8

Repeated Shampoo Washing Deposition Behavior

| | ΔE After Each Wash vs. Before Each Wash | |
|---|---|---|
| Shampoo Wash # | Polymeric Colorant (Example 10) | Comparative Dye Example Ext. D&C Violet 2 |
| 1 | 4.7 | 4.3 |
| 2 | 2.0 | 2.5 |
| 3 | 2.5 | 1.5 |
| 4 | 0.9 | 1.7 |
| 5 | 0.4 | 1.8 |

Application Example 7

Many different shampoo formulations can be used to deliver polymeric colorants onto hair. This was demonstrated by taking a single polymeric colorant (Example 2) and mixing it into several different commercial shampoo formulations at 0.65% by mass and applied to bleached blonde hair. The amount of shampoo used was 0.2 grams of shampoo per gram of hair. The shampoo was contacted with the hair 3 minutes before rinsing off. The amount of color deposited onto the hair was evaluated by measure ΔE of the washed hair relative to the unwashed, uncolored hair and is shown in Table 9.

There were seven different shampoos evaluated, each with different ingredients in the shampoos. Free & Clear Shampoo for Sensitive Skin (Pharmaceutical Specialties, Inc.) contained Purified Water, Lauryl Glucoside, Coco-Glucoside, Acrylates Copolymer, Disodium Cocoyl Glutamate, Sodium Cocoyl Glycinate, Glycerin, Sucrose Cocoate, Panthenol, Pentylene Glycol, 1,2-Hexanediol, Sodium Cocoyl Glutamate, Disodium EDTA, Caprylyl Glycol, Sodium Hydroxide, Sodium Chloride. After Color Treatment Shampoo (Fanola) contained Aqua (Water), Ammonium Lauryl Sulfate, Sodium Myreth Sulfate, Sodium Cocoamphoacetate, Sodium Chloride, Glycol Distearate, Sodium Laureth Sulfate, Parfum (Fragrance), Cocamide MEA, Citric Acid, Guar Hydroxypropyltrimonium Chloride, Laureth-10, Hydrolyzed Wheat Protein, Triethylene Glycol, Benzyl Alcohol, Propylene Glycol, Tocopheryl Acetate, Sodium Benzoate, Phenoxyethanol, Methylchloroisothiazolinone Methylisothiazolinone, *Linum Usitatissimum* Seed Oil (Linseed Seed Oil), Magnesium Nitrate, Magnesium Chloride. Tresemme Pro Pure Micellar Moisture Shampoo (Unilever) contained Water (aqua), Cocamidopropyl Betaine, Sodium Methyl Cocoyl Taurate, Sodium Chloride, Fragrance (Parfum), Sodium Benzoate, Citric Acid, Coconut Acid, Polyquaternium-10, Stearamidopropyl Dimethylamine, Disodium EDTA, PPG-9, Benzyl Salicylate, Hexyl Cinnamal, Limonene, Linalool. Schauma 7 Herbs Shampoo (Schwarzkopf) contained Aqua, Sodium Laureth Sulfate, Sodium Chloride, Cocamidopropyl Betaine, Hydrolyzed Soy Protein, Niacinamide, Magnesium Chloride, *Chamomilla Recutita* Flower Extract, *Salvia officinalis* Leaf Extract, *Melissa officinalis* Leaf Extract, *Urtica dioica* Extract, *Equisetum arvense* Extract, *Rosmarinus officinalis* Leaf Extract, *Humulus lupulus* Extract, *Simmondsia chinensis* Seed Oil, Disodium Cocoamphodiacetate, PEG-7 Glyceryl Cocoate, Sodium Benzoate, Cocamide MEA, Citric Acid, Glycol Distearate, Parfum, Laureth-4, Hydrogenated Castor Oil, PEG-40 Hydrogenated Castor Oil, Polyquaternium-10, Linalool, Benzyl Alcohol, Propylene Glycol, Hexyl Cinnamal, CI 47005, CI 42090. Pantene Nutrient Blends Illuminating Color Care Shampoo (P&G) contained Water, Lauramidopropyl Betaine, Sodium Cocoyl Isethionate, Sodium Lauroyl Sarcosinate, Sodium Citrate, Citric Acid, Fragrance, Sodium Benzoate, Sodium Salicylate, Polyquaternium-10, Dimethiconol, Tetrasodium EDTA, Panthenol, Panthenyl Ethyl Ether, Histidine, Biotin. BC Bonacure pH 4.5 Color Freeze Micellar Rich Shampoo (Schwarzkopf) contained Aqua (Water, Eau) Sodium Laureth Sulfate, Lactic Acid, Cocamidopropyl Betaine, Cocamide MEA, Hydrolyzed Keratin, Steardimonium Hydroxypropyl Hydrolyzed Keratin, *Prunus Armeniaca* (Apricot) Kernel Oil, Panthenol, PEG-12 Dimethicone, Disodium Cocoamphodiacetate, PEG-7 Glyceryl Cocoate, Polyquaternium-10, Calcium Hydroxide, sodium Benzoate, Sodium Chloride, Parfum (Fragrance), Glycol Distearate, PEG-40 Hydrogenated Castor Oil, Laureth-4, Hydrogenated Castor Oil, PEG-120 Methyl Glucose Dioleate, PEG-12 Allyl Ether, Benzophenon-4, PEG-12, Mica, Benzyl Salicylate, Butylphenyl Methylpropional, Linalool Limonene, Propylene Glycol, Calcium Carbonate, C177891 (Titanium Dioxide), CI 17200 (Red 33). EverPure Blonde Shampoo (L'Oreal) contained Aqua/Water/Eau, Coco-Betaine, Disodium Laureth Sulfosuccinate, Sodium Cocoyl Isethionate, Sodium Lauryl Sulfoacetate, Sodium Lauroyl Sarcosinate, Glycol Distearate, Sodium Chloride, Decyl Glucoside, Parfum/Fragrance, Polyquaternium-10, Amodimethicone, PPG-5-Ceteth-20, Propylene Glycol, PEG-55 Propylene Glycol Oleate, Hydrogenated Coconut Acid, Carbomer, Sodium Hydroxide, Acrylates/Beheneth-25 Methacrylate Copolymer, Benzophenone-4, Sodium Isethionate, Butylene Glycol, Benzoic Acid, Trideceth-6, Linalool, Hydroxycitronellal, Sodium Acetate, Cetrimonium Chloride, Sodium Benzoate, Isopropyl Alcohol, Iris Florentina Root Extract, *Calendula officinalis* Flower Extract, Methylchloroisothiazolinone, C160730/EXT. Violet 2, Magnesium Chloride, Methylisothiazolinone, CI 17200/Red 33, Citric Acid.

The polymeric colorant shows deposition in all the evaluated shampoos which demonstrates these materials will work in a wide range of different formulations, each with a wide variety of ingredients. The shampoos have a variety of different surfactant including some with no sulfates or betaines and a variety of different other additives such as cationic additives, silicones, etc. While there is some variation in performance across different formulations, the relative change is generally small.

TABLE 9

Single Application Deposition Performance of a Polymeric Colorant (Example 2) in Different Shampoo Formulations

| Shampoo | ΔE | ΔYI |
| --- | --- | --- |
| Free & Clear Shampoo for Sensitive Skin | 8.7 | −13 |
| After Color Treatment Shampoo | 8.6 | −13 |
| Tresemme Pro Pure Micellar Moisture Shampoo | 8.5 | −12 |
| Schauma 7 Herbs Shampoo | 7.7 | −11 |
| Illuminating Color Care with Biotin Shampoo | 7.5 | −10 |
| BC Bonacure pH 4.5 Color Freeze Shampoo | 6.3 | −8 |
| EverPure Blonde Shampoo | 6.1 | −8 |

Application Example 8

It is also desirable to color or tone hair using other hair care compositions. Conditioner is a commonly used hair care composition that can also be used to deposit color onto hair. A range of polymeric colorants can be used to color hair in a conditioner formulation. The hair care composition in this example was a conditioner, EverPure Blonde Conditioner (L'Oreal). For each colorant, the amount of colorant in the conditioner was adjusted so that each sample exhibited the same color strength, meaning the amount of chromophore or absorbance in each conditioner was the same despite the different polymer chain lengths and chromophore types. The maximum absorbance of the colored conditioner was 0.25 when measured with 1 cm path length at concentration of 1 grams/liter in methanol. For this study, bleached blonde hair was used as the hair substrate and the hair was colored using the procedure above. The amount of conditioner used was 0.2 grams of conditioner per gram of hair. The conditioner was contacted with the hair 3 minutes before rinsing off. To evaluate the amount of color deposited onto the hair, the ΔE value for the post conditioner vs. the pre-conditioner hair was used.

In addition, the Yellowness Index (YI) was calculated for the post conditioner and the pre-conditioner as described before. In addition to the polymeric colorants evaluated for conditioner, a commercial dye commonly used in conditioner was also included as a comparative sample. External D&C Violet 2 (also known as Acid Violet 43) was formulated identically to the polymeric colorants in terms of absorbance per gram of conditioner. Results are shown in Table 10. Unexpectedly, all of the evaluated polymeric colorants show greater deposition onto the hair in conditioner than the commonly used dye, Ext. D&C Violet 2. The ΔYI is also more strongly negative than the comparative dye, implying that they are more effective at neutralizing yellow tones. Also unexpectedly, several polymeric colorants show much higher deposition out of conditioner than shampoo. Example 1 shows 13 times greater ΔE in conditioner than in shampoo (see Table 7); similarly, Example 2 shows over double the ΔE in conditioner that it showed in shampoo. The polymeric colorants show very good blending into the conditioner due to their liquid nature.

TABLE 10

Single Application Deposition Performance in Conditioner for Different Polymeric Colorants

| Cream | ΔE | ΔYI |
| --- | --- | --- |
| Comparative Dye Example Ext. D&C Violet 2 | 3.4 | −4.0 |
| Example 33 | 18.7 | −21.8 |
| Example 1 | 16.9 | −24.1 |
| Example 2 | 14.8 | −22.4 |

Application Example 9

Many different conditioner formulations can be used to deliver polymeric colorants onto hair. This was demonstrated by taking a single polymeric colorant (Example 1) and mixing it into several different commercial conditioner formulations at 1% by mass and applied to bleached blonde hair. The amount of conditioner used was 0.2 grams of conditioner per gram of hair. The conditioner was contacted with the hair 3 minutes before rinsing off. The amount of color deposited onto the hair was evaluated by measure ΔE of the post-conditioner hair relative to the unconditioned, uncolored hair and is shown in Table 11.

There were four different conditioners evaluated, each with different ingredients in the conditioners. Pantene Pro-V Classic Clean Conditioner (P&G) contained Water, Stearyl Alcohol, Stearamidopropyl Dimethylamine, Cetyl Alcohol, Glutamic Acid, Fragrance, Bis-Aminopropyl Dimethicone, Benzyl Alcohol, Citric Acid, Disodium EDTA, Histidine, Panthenol, Panthenyl Ethyl Ether, Methylchloroisothiazolinone, Methylisothiazolinone. Pantene Nutrient Blends Illuminating Color Care Conditioner (P&G) contained Water, Stearyl Alcohol, Silicone Quaternium-26, Behentrimonium Chloride, Cetyl Alcohol, Fragrance, Benzyl Alcohol, Disodium EDTA, Panthenol, Panthenyl Ethyl Ether, Histidine, Citric Acid, Sodium Hydroxide, Biotin, Methylchloroisothiazolinone, Methylisothiazolinone. Nutri Care Restructuring Conditioner (Fanola) contained Water, Stearyl Alcohol, Silicone Quaternium-26, Behentrimonium Chloride, Cetyl Alcohol, Fragrance, Benzyl Alcohol, Disodium EDTA, Panthenol, Panthenyl Ethyl Ether, Histidine, Citric Acid, Sodium Hydroxide, Biotin, Methylchloroisothiazolinone, Methylisothiazolinone. EverPure Blonde Conditioner (L'Oreal) contained Aqua/Water/Eau, Cetearyl Alcohol, Glycerin, Behentrimonium Chloride, Cetyl Esters, Isopropyl Myristate, Propylene Glycol Quaternium-80, Parfum/Fragrance, Polysorbate 20, Isopropyl Alcohol, Phenoxyethanol, Polyquaternium-37, Paraffinum Liquidum/Mineral Oil/Huile Minerale, Tocopherol Acetate, Butylenr Glycol, Linalool, Chlorhexidine Dihydrochloride, Citric Acid, Ppg-1 Trideceth-6, Hexyl Cinnamal, Hydroxycitronellal, Acrylates Copolymer, Sorbitan Oleate, Iris Florentina Root Extract, *Calendula officinalis* Flower Extract, C160730/EXT. Violet 2, C117200/Red 33, BHT.

In this case, where was some difference in performance between certain conditioners, but the polymeric colorant shows strong deposition in all the evaluated conditioners. This demonstrates these materials will work in a wide range of different formulations, each with a wide variety of ingredients.

TABLE 11

Single Application Deposition Performance of a Polymeric Colorant (Example 1) in Different Conditioner Formulations

| Cream | ΔE | ΔYI |
|---|---|---|
| Pantene Pro-V Classic Clean Cond. (P&G) | 22.8 | −33 |
| Pantene Illuminating Color Care Cond. (P&G) | 21.7 | −31 |
| Nutri Care Restructuring Conditioner (Fanola) | 16.9 | −26 |
| EverPure Blonde Conditioner (L'Oreal) | 16.5 | −24 |

Application Example 10

The examples above demonstrate the unexpected advantages and differences for polymeric colorants compared to conventional hair dyes. Assuming the colorants are fully dissolved into the cream, one might expect that they would have poor stability in certain hair care products, especially in an oxidative hair cream containing hydrogen peroxide. Surprisingly, several examples of this type of polymeric colorant which were stable in an oxidative cream containing 12% hydrogen peroxide were discovered, as described below.

Several polymeric colorants were tested for stability and coloring performance in a commercially available oxidative hair cream. Each sample was added to Fanola 40 Vol Perfumed Cream Developer (available from Fanola of Italy), which contained about 12% hydrogen peroxide. Each sample was mixed using a SpeedMixer at 1500 rpm until a visually uniform mixture was obtained (a minimum of 90 seconds; SpeedMixer from Inc., Landrum, SC). The amount of color contained in each sample was adjusted so that each sample exhibited the same color strength. The maximum absorbance of the colored cream was 0.67 when measured with 1 cm path length at concentration of 1 gram/liter in methanol. After mixing, the samples were stored first at room temperature for 7 days and then moved to a 40° C. oven. The stability of color was evaluated by the room temperature equivalent days it takes to reach 50% loss of color based the original measured color in the cream at time zero as measured by UV-VIS. Loss of color is de-coloration due to chemical changes in colorant from the oxidative cream ingredients including peroxide. Many of these colorants evaluated were stable in the oxidative emulsion as shown below in Table 13.

The room temperature equivalent days was calculated by the following equation:

Room temperature equivalent days=Days stored at room temperature+Days stored at 40° C.*3.48

Using the room temperature equivalent days for the color to degrade to 50%, a rating was generated according to the table below. A value of "1" indicated the composition was most stable, while a value of "5" indicated that it was the least stable.

TABLE 12

Rating Scale for Stability of Oxidative Hair Cream Containing Polymeric Colorant

| Rating | Room temperature equivalent days to 50% |
|---|---|
| 1 | More than 300 days |
| 2 | From 150 to 300 days |
| 3 | From 50 to 150 days |
| 4 | From 20 to 50 days |
| 5 | Less than 20 days |

TABLE 13

Stability of Inventive Polymeric Colorants in Oxidative Hair Cream

| Polymeric Colorant | Rating |
|---|---|
| Example 1 | 1 |
| Example 37 | 1 |
| Example 18 | 2 |
| Example 10 | 1 |

Application Example 11

In addition to strongly coloring the hair to bright colors such as blue, red, yellow, there is also a desire to controllably deposit a less noticeable amount of certain colors to neutralize the spectrum of undertones that are exposed during the a hair bleaching or lightening process. Light brown hair, for example, would expose yellow undertones upon bleaching. Therefore, according to the law of color, a violet-based toner would neutralize the yellowish hue to result in a platinum or silver blond shade. The concentration of the toner may be adjusted so that the lift is not masked by the deposition of color. In accordance with present invention, there is a single-step process using a composition of hair bleach that can simultaneously lighten the hair and effectively deposit various shades of color. This is achieved by including dyes in the bleach composition. As demonstrated above, several of the blue and violet polymeric colorants show good stability in oxidative cream, so one can pre-mix a violet colorant into an oxidative hair cream and then simultaneously lighten hair while depositing the colorant to neutralizes the unwanted yellow tones. This is demonstrated below.

Materials:
Blonde Hair (lightly bleached dark hair), cut to 3 cm wide, 20 cm long
Fanola Violet Bleach Powder
Fanola 40 Vol. (12% peroxide) oxidative cream Procedure:
The hair was weighed first in order to calculate the amount of cream needed (4 grams of cream per gram of hair). Color and oxidative cream developer were mixed as described above. The mixtures were checked and remixed when necessary to ensure the color was fully homogenous. Fanola Violet Bleach Powder (available from Fanola of Italy) was weighed into a small weigh boat (two parts cream to one part bleach powder). The appropriate amount of oxidative cream was added to the bleach powder. Using the wooden end of a cotton-tipped applicator, the bleach/cream was stirred until fully mixed. The bleach/cream mixture was transferred to a large weigh boat with the hair sample. The mixture was spread all over the hair and worked into the hair with fingertips until the mixture was fully incorporated evenly throughout the hair. The bleach was allowed to sit on the hair for 15 minutes and then the hair sample was rinsed thoroughly with lukewarm water, combed, and dried in the oven at 60° C. for 45 minutes. The color of hair was measured using the X-Rite Color-eye with a 6 mm aperture, with D-65 light source. The hair was twisted tight and pressed to the aperture while taking the measurement. An average of 6-8 measurements was used.

As described earlier, the Yellowness Index (YI) was calculated for each sample. The YI is good indicator for how well the hair was lightened and toned. The initial hair had a whiteness index (YI) of 48.9 due to its yellow color. After treatment, the YI values decreased, indicating the hair was lightened. The differences of the YI between treated hair and initial hair, ΔYI, were recorded. Larger, more negative, ΔYI indicate better lightening of the hair.

The YI and ΔYI values of the initial hair, bleach control (no dye), and bleach composition containing Example 1 and Comparative Example External D&C Violet 2 are shown in Table 14. The bleach composition with Example 1 provided better lightening than the bleach control and bleach with Comparative Example External D&C Violet 2.

TABLE 14

Color Evaluation for Simultaneously Bleaching and Toning Hair

| Sample | YI Value | ΔYI Value |
|---|---|---|
| Initial Hair | 48.9 | n/a |
| Bleach Control | 43.8 | −5.1 |
| Bleach with Example 1 | 39.3 | −9.6 |
| Bleach with Comparative Example External D&C Violet 2 | 42.1 | −6.9 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:
1. A method for coloring human head or facial hair comprising the following steps:
(a) providing a hair care composition that contains at least one poly(alkyleneoxy) substituted chromophore colorant, wherein the chromophore of the colorant is selected from azo, carbazole, pyrazolone, cyanine, phthalocyanine, aza[18]annulene, formazan copper complex, nitroso, nitro, diarylmethane, triarylmethane, xanthene, acridine, methine, thiazole, indamine, azine, oxazine, thiazine, quinoline, indigoid, indophenol, lactone, aminoketone, hydroxyketone, naphthalimide, and stilbene chromophores;
(b) applying the hair care composition to hair; and
(c) allowing the hair care composition to contact the hair for a period of time.
2. The method of claim 1, wherein the hair care composition additionally contains at least one hair care ingredient.
3. The method of claim 1, wherein the method further comprises removing the hair care composition from the hair.
4. The method of claim 1, wherein the poly(alkyleneoxy) substituted chromophore colorant is present in a concentration of from 0.001 to 20 wt. % of the composition.
5. The method of claim 1, wherein the poly(alkyleneoxy) substituted chromophore colorant is present in a concentration of from 0.01 to 20 wt. % of the composition.

6. The method of claim 1, wherein the poly(alkyleneoxy) substituent of the said chromophore colorant is a polymeric group comprised of alkyleneoxide residues having from 2 to 4 carbon atoms.

7. The method of claim 1, wherein the average molecular weight of the poly(alkyleneoxy) substituent is from 132 to 10,000.

8. The method of claim 1, wherein the at least one poly(alkyleneoxy) substituted chromophore colorant has a structure of:

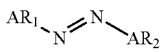

wherein $AR_1$ and $AR_2$ are independently selected from the group consisting of alkenyl groups, substituted alkenyl groups, aryl groups, substituted aryl groups, heteroaryl groups, and substituted heteroaryl groups; wherein one of the $AR_1$ or $AR_2$ group is optionally further substituted with another azo chromophore to form a bis azo.

9. The method of claim 8, wherein the substituted heteroaryl group is a substituted thiazolium group.

10. The method of claim 1, wherein the at least one poly(alkyleneoxy) substituted chromophore colorant has the following structure:

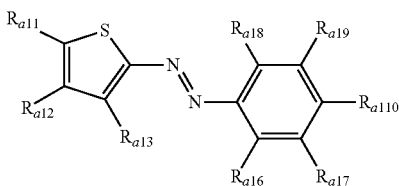

wherein each $R_{a11}$ to $R_{a110}$ group is independently selected from the group consisting of hydrogen, deuterium, —CN and $R^v$; each $R^v$ is independently selected from the group consisting of halogens, nitro, nitrile, alkyl, substituted alkyl, alkenyl, substituted alkenyl, aryl, substituted aryl, alkynyl, substituted alkynyl, —$(CH_2)_n$—O—$R^x$, —$(CH_2)_n$—$NR^xR^y$, —C(O)$R^x$, —C(O)O$R^x$, —C(O)O$^-$, —C(O)$NR^xR^y$, —OC(O)$R^x$, —OC(O)O$R^x$, —OC(O)$NR^xR^y$, —S(O)$_2R^x$, —S(O)$_2OR^x$, —S(O)$_2$O, —S(O)$_2NR^xR^y$, —$NR^xC(O)R^y$, —$NR^xC(O)OR^y$, —$NR^xC(O)SR^y$, —$NR^xC(O)NR^yR^z$, —O$R^x$, —$NR^xR^y$, —P(O)$_2R^x$, —P(O)(O$R^x$)$_2$, —P(O)(O$R^x$)O$^-$, and —P(O)(O$^-$)$_2$; wherein the index n is an integer from 0 to 4; and wherein $R^x$, $R^y$ and $R^z$ are independently selected from the group consisting of hydrogen, alkyl, substituted alkyl, alkenyl, substituted alkenyl, aryl, substituted aryl, alkynyl, substituted alkynyl, and $R^u$; $R^u$ is an organic group composed of one or more organic monomers with said one or more organic monomers having molecular weights ranging from 28 to 500.

11. The method of claim 10, wherein at least one of the $R_{a11}$, $R_{a12}$, and $R_{a13}$ is an electro-withdrawing group selected from —CN, halogens, nitro, nitrile, —C(O)$R^x$, —C(O)O$R^x$, —C(O)$NR^xR^y$, —OC(O)$R^x$, —OC(O)O$R^x$, —OC(O)$NR^xR^y$, —S(O)$_2R^x$, —S(O)$_2OR^x$, —P(O)$_2R^x$, and —P(O)(O$R^x$)$_2$ groups.

12. The method of claim 11, wherein the $R_{a11}$ and $R_{a13}$ groups are —CN, and $R_{a12}$ is a methyl group.

13. The method of claim 12, wherein $R_{a16}$, $R_{a17}$, $R_{a18}$, $R_{a19}$, $R_{a110}$ are independently selected from hydrogen, halogens, methyl group, ethyl groups, propyl groups, isopropyl group, n-butyl group, isobutyl groups, 2-butyl groups, tert-butyl groups, —$(CH_2)_n$—O—$R^x$, —$(CH_2)_n$—$NR^xR^y$, —O$R^x$, and —$NR^xR^y$, and at least one of $R_{a16}$, $R_{a17}$, $R_{a18}$, $R_{a19}$, $R_{a110}$ is —O$R^x$, or —$NR^xR^y$.

14. The method of claim 12, wherein two or more of $R_{a16}$, $R_{a17}$, $R_{a18}$, $R_{a19}$, $R_{a110}$ are connected to each other through covalent bonds to form a ring structure fused with the benzene ring in Formula I-A.

15. The method of claim 14, wherein the ring structure fused with the benzene ring in Formula I-A forms one of naphthalene, tetrahydroquinoline, tetrahydroisoquinoline, indoline, and isoindoline.

16. The method of claim 15, wherein the ring structure is substituted by one or more of hydrogen, halogens, methyl group, ethyl groups, propyl groups, isopropyl group, n-butyl group, isobutyl groups, 2-butyl groups, tert-butyl groups, —$(CH_2)_n$—O—$R^x$, —$(CH_2)_n$—$NR^xR^y$, —O$R^x$, and —$NR^xR^y$.

17. The method of claim 13, wherein two of $R^x$, $R^y$, or $R^z$ are attached to the same carbon or nitrogen group and form the ring structure.

18. The method of claim 17, wherein the ring structure is one of piperazine, piperidine, and pyrrolidine.

19. The method of claim 18, wherein the ring structure is further substituted by one or more of hydrogen, halogens, methyl group, ethyl groups, propyl groups, isopropyl group, n-butyl group, isobutyl groups, 2-butyl groups, tert-butyl groups, —$(CH_2)_n$—O—$R^x$, —$(CH_2)_n$—$NR^xR^y$, —O$R^x$, and —$NR^xR^y$.

20. The method of claim 13, wherein the colorant is a thiophene azo colorant according to the following structure:

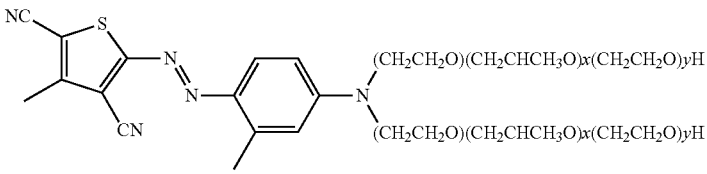

wherein each x and y are independently integers from 0 to 20.

21. The method of claim 1, wherein the at least one poly(alkyleneoxy) substituted chromophore colorant has a structure selected from:

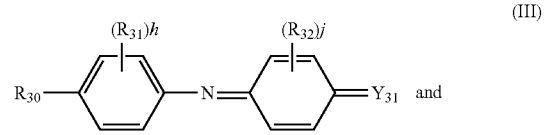

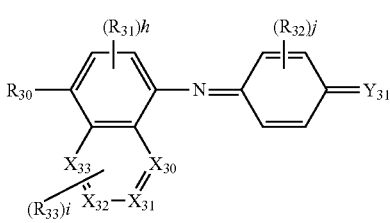

wherein h, i, and j are independently integers from 0 to 4; provided in structure IIIa h is an integer from 0 to 2; $Y_{31}$ is selected from the group consisting of =O, =S, =NR$_{34}$, and =N$^+$R$_{34}$R$_{35}$; $R_{30}$ is selected from the group consisting of —O—, —S$^-$, —OR$_{36}$ and —NR$_{36}$R$_{37}$; each $R_{34}$, $R_{35}$, $R_{36}$ and $R_{37}$ is independently selected from the group consisting of hydrogen, alkyl groups, substituted alkyl groups, aryl groups, substituted aryl groups, heteroaryl group, substituted heteroaryl group, acyl groups, —C(O)OR$_5$, —C(O)R$_5$, and —C(O)NR$_5$R$_6$; each $R_{31}$, $R_{32}$ and $R_{33}$ group is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O) OR$_5$, —C(O)R$_5$, —C(O)NR$_5$R$_6$, —NR$_5$C(O) OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups; $X_{30}$, $X_{31}$, $X_{32}$, and $X_{33}$ are independently selected from the group consisting of a carbon atom and a nitrogen atom, provided no more than two of $X_{30}$, $X_{31}$, $X_{32}$, and $X_{33}$ are nitrogen atoms.

22. The method of claim 1, wherein the at least one poly(alkyleneoxy) substituted chromophore colorant has a structure of:

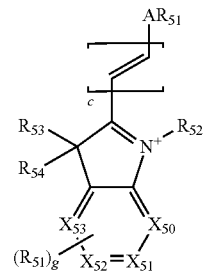

wherein $X_{42}$ is selected from the group consisting of an oxygen atom, a sulfur atom, SiR$_{45}$R$_{46}$, and NR$_{45}$; $Y_{41}$ is selected from the group consisting of =O, =S, =NR$_{46}$, and =N$^+$R$_{45}$R$_{46}$; $R_{45}$ and $R_{46}$ is selected from the group consisting of hydrogen, alkyl groups, substituted alkyl groups, aryl groups, substituted aryl groups, heteroaryl group, substituted heteroaryl group, —S(O)$_2$OH, —S(O)$_2$O$^-$[M$^+$], —C(O)OR$_5$, —C(O)R$_5$, and —C(O) NR$_5$R$_6$; l is an integer from 0 to 3 and m is an integer from 0 to 4; each $R_{41}$ and $R_{42}$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —SR$_5$, —S(O)$_2$NR$_5$R$_6$, and —P(O)$_2$R$_5$; M is a cation; wherein at least one $R_{42}$ group is selected from the group consisting of —OR$_5$, —SR$_5$ and —NR$_5$R$_6$; $R_5$ and $R_6$ are independently selected from the group consisting of hydrogen, alkyl groups, substituted alkyl groups, aryl groups, and substituted aryl groups.

23. The method of claim 1, wherein the at least one poly(alkyleneoxy) substituted chromophore colorant has a structure of:

V wherein AR$_{51}$ is selected from the group consisting of alkenyl groups, substituted alkenyl groups, aryl groups, substituted aryl groups, heteroaryl groups, substituted heteroaryl groups; $R_{52}$ $R_{53}$ and $R_{54}$ are independently selected from the group consist of hydrogen and $R_{51}$; each $R_{51}$ is independently selected from halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O) SR$_6$, —OR$_5$, —NR$_5$R$_6$, —S(O)$_2$R$_5$, —S(O)$_2$NR$_5$R$_6$, and —P(O)$_2$R$_5$, M is a cation, provided $R_{51}$ is not a hydrogen; $R_5$ and $R_6$ are independently selected from the group consisting of hydrogen, alkyl groups, substituted alkyl groups, aryl groups, and substituted aryl groups; c is an integer from 1 to 10; $X_{50}$, $X_{51}$, $X_{52}$, and $X_{53}$ are independently selected from the group consisting of a carbon atom and a nitrogen atom, provided no more than two of $X_{50}$, $X_{51}$, $X_{52}$, and $X_{53}$ are nitrogen atoms; g is an integer from 1 to 4; wherein the structure V optionally is present in an ionic form that accompanies its counter ion to maintain electric neutrality.

24. The method of claim 1, wherein the at least one poly(alkyleneoxy) substituted chromophore colorant has a structure of:

VI wherein each $R_{61}$, $R_{62}$, $R_{63}$, and $R_{64}$ group is independently selected halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4; $R_5$ and $R_6$ are independently selected from the group consisting of hydrogen, alkyl groups, substituted alkyl groups, aryl groups, and substituted aryl groups; Q is hydrogen, metal ion, or metalloids; A is an anion; x is a positive integer, and y is an integer including zero so that the divalent group -Q$_x$A$_y$- is neutral.

25. The method of claim 1, wherein the at least one poly(alkyleneoxy) substituted chromophore colorant has a structure of:

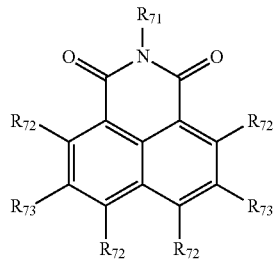

VII wherein each $R_{71}$, $R_{72}$ and $R_{73}$ group is independently selected hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)NR$_6$NR$_7$R$_8$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; wherein n, o, p and q are integers independently select from 0 to 4; $R_5$, $R_6$, $R_7$ and $R_8$ are independently selected from the group consisting of hydrogen, alkyl groups, substituted alkyl groups, aryl groups, and substituted aryl groups, provided at least one $R_{72}$ groups is —OR$_5$ or —NR$_5$R$_6$ group.

26. The method of claim 1, wherein the at least one poly(alkyleneoxy) substituted chromophore colorant has a structure selected from:

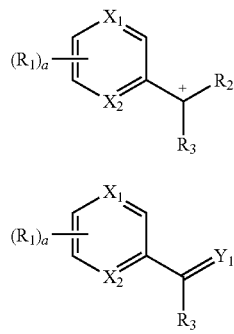

VIII

VIIIa wherein $X_1$ and $X_2$ are selected from the group consisting of a carbon atom and a nitrogen atom; a is an integer from 0 to 5, provided a is an integer from 0 to 4 when one of $X_1$ and $X_2$ is a nitrogen atom and a is an integer from 0 to 3 when both $X_1$ and $X_2$ are nitrogen atoms; each $R_1$ is independently selected from the group consisting of halogen, hydroxy group, nitro group, nitrile group, alkyl group, substituted alkyl group, alkenyl group, substituted alkenyl group, aryl group, substituted aryl group, heteroaryl group, and substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups; $R_2$ and $R_3$ is selected from the group consisting of alkenyl groups, substituted alkenyl groups, aryl groups, substituted aryl groups, heteroaryl groups, and substituted heteroaryl groups; $Y_1$ is selected from the group consisting of =O, =S, =NR$_5$, and =N$^+$R$_5$R$_6$; wherein the structure VIII and VIIIa independently and optionally exist in an ionic form that accompanies its counter ion to maintain electric neutrality.

27. The method of claim 1, wherein the at least one poly(alkyleneoxy) substituted chromophore colorant has a structure of:

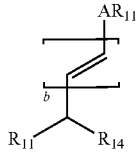

IX wherein AR$_{11}$ is selected from the group consisting of alkenyl groups, substituted alkenyl groups, aryl groups, substituted aryl groups, heteroaryl groups, and substituted heteroaryl groups; $R_{11}$ and $R_{14}$ are independently selected from the group consist of hydrogen, halogen, hydroxy group, nitro group, nitrile group, alkyl group, substituted alkyl group, alkenyl group, substituted alkenyl group, aryl group, substituted aryl group, heteroaryl group, substituted heteroaryl group, —S(O)$_2$OH, —S(O)$_2$O$^-$[M$^+$], —C(O)OR$_5$, —C(O)R$_5$, —C(O)NR$_5$R$_6$, —NR$_5$C(O)OR$_6$, —NR$_5$C(O)SR$_6$, —OR$_5$, —NR$_5$R$_6$, —S(O)$_2$R$_5$, —S(O)$_2$NR$_5$R$_6$, and —P(O)$_2$R$_5$; M is a cation; $R_5$ and $R_6$ are independently selected from the group consisting of hydrogen, alkyl groups, substituted alkyl groups, aryl groups, and substituted aryl groups; b is an integer from 1 to 10.

28. The method of claim 1, wherein at least 50 molar % of the poly(alkyleneoxy) substituted chromophore colorant has a molecular weight less than 5000.

29. The method of claim 28, wherein the poly(alkyleneoxy) substituted chromophore colorants contain monomer residues, and wherein at least 75% of the monomer residues in the poly(alkyleneoxy) substituent are selected from —CH$_2$CH$_2$O— and —CH$_2$CH(CH$_3$)O—.

30. The method of claim 1, wherein at least 50 molar % of the poly(alkyleneoxy) substituted chromophore colorant has a molecular weight less than 2000.

31. The method of claim 30, wherein the poly(alkyleneoxy) substituted chromophore colorants contain monomer residues, and wherein at least 75% of monomer residues in the poly(alkyleneoxy) substituent are —CH$_2$CH$_2$O—.

32. The method of claim 1, wherein the hair care composition is a non-oxidative hair coloring cream.

33. The method of claim 32, wherein the non-oxidative hair coloring cream is a semi-permanent hair coloring cream.

34. The method of claim 32, wherein the non-oxidative hair coloring cream is a temporary hair coloring cream.

35. The method of claim 1, wherein the hair care composition is an oxidative hair coloring cream.

36. The method of claim 35, wherein the oxidative hair coloring cream is a demi-permanent hair coloring cream.

37. The method of claim 36, wherein the oxidative hair coloring cream is a permanent hair coloring cream.

38. The method of claim 1, wherein the hair care composition is a shampoo.

39. The method of claim 1, wherein the hair care composition is a conditioner.

* * * * *